(12) United States Patent
Nagao et al.

(10) Patent No.: US 11,696,814 B2
(45) Date of Patent: Jul. 11, 2023

(54) MEDICAL ARM SYSTEM, CONTROL DEVICE, AND CONTROL METHOD

(71) Applicant: SONY CORPORATION, Tokyo (JP)

(72) Inventors: Daisuke Nagao, Kanagawa (JP);
Toshimitsu Tsuboi, Tokyo (JP);
Yasuhiro Matsuda, Tokyo (JP);
Tetsuharu Fukushima, Tokyo (JP)

(73) Assignee: SONY CORPORATION, Tokyo (JP)

( * ) Notice: Subject to any disclaimer, the term of this patent is extended or adjusted under 35 U.S.C. 154(b) by 963 days.

(21) Appl. No.: 16/485,615

(22) PCT Filed: Feb. 16, 2018

(86) PCT No.: PCT/JP2018/005465
§ 371 (c)(1),
(2) Date: Aug. 13, 2019

(87) PCT Pub. No.: WO2018/159328
PCT Pub. Date: Sep. 7, 2018

(65) Prior Publication Data
US 2019/0365499 A1 Dec. 5, 2019

(30) Foreign Application Priority Data

Feb. 28, 2017 (JP) ................................ 2017-036842
Feb. 28, 2017 (JP) ................................ 2017-036843

(51) Int. Cl.
*A61B 34/20* (2016.01)
*A61B 34/30* (2016.01)
*A61B 90/50* (2016.01)
(Continued)

(52) U.S. Cl.
CPC .......... *A61B 90/50* (2016.02); *A61B 1/00149* (2013.01); *A61B 34/30* (2016.02);
(Continued)

(58) Field of Classification Search
CPC ... A61B 34/70; A61B 90/50; A61B 2034/301; B25J 13/00; G02B 23/24
See application file for complete search history.

(56) References Cited

U.S. PATENT DOCUMENTS

2005/0033117 A1* 2/2005 Ozaki .................... A61B 1/045
600/117
2015/0119637 A1* 4/2015 Alvarez ................. A61B 34/71
600/102
(Continued)

FOREIGN PATENT DOCUMENTS

| CN | 105188594 A | 12/2015 |
|---|---|---|
| CN | 105939547 A | 9/2016 |

(Continued)

OTHER PUBLICATIONS

International Search Report and Written Opinion of PCT Application No. PCT/JP2018/005465, dated Apr. 24, 2018, 11 pages of ISRWO.

(Continued)

*Primary Examiner* — Jon Eric C Morales
(74) *Attorney, Agent, or Firm* — Chip Law Group

(57) ABSTRACT

Proposed is a mechanism capable of securing both convenience and safety in regard to surgery performed by inserting an endoscope into a human body. A medical arm system including a multi-joint arm which has a plurality of links connected by joints and a distal end to which an endoscope is connectable and a control unit which sets a virtual plane in a body cavity of a patient and controls the multi-joint arm so as to constrain a predetermined point of the endoscope in the body cavity on the virtual plane.

19 Claims, 22 Drawing Sheets

(51) Int. Cl.
   *A61B 34/00* (2016.01)
   *A61B 90/00* (2016.01)
   *A61B 1/00* (2006.01)
   *A61B 17/00* (2006.01)

(52) U.S. Cl.
   CPC ............ *A61B 34/70* (2016.02); *A61B 90/361* (2016.02); *A61B 17/00234* (2013.01); *A61B 2034/301* (2016.02); *A61B 2034/305* (2016.02)

(56) References Cited

U.S. PATENT DOCUMENTS

| | | |
|---|---|---|
| 2016/0066768 A1 | 3/2016 | Popovic et al. |
| 2016/0100898 A1 | 4/2016 | Jinno et al. |
| 2017/0080574 A1 | 3/2017 | Kuroda et al. |

FOREIGN PATENT DOCUMENTS

| | | |
|---|---|---|
| CN | 105939647 A | 9/2016 |
| CN | 105979897 A | 9/2016 |
| CN | 106132346 A | 11/2016 |
| CN | 111166274 A | 5/2020 |
| EP | 3135445 A1 | 3/2017 |
| EP | 3590405 A1 | 1/2020 |
| JP | 2000-166857 A | 6/2000 |
| JP | 2001-275931 A | 10/2001 |
| JP | 2003-310638 A | 11/2003 |
| JP | 2007-029232 A | 2/2007 |
| JP | 2016-524487 A | 8/2016 |
| WO | 2014/181222 A1 | 11/2014 |
| WO | 2014/199413 A1 | 12/2014 |
| WO | 2015/146850 A1 | 10/2015 |

OTHER PUBLICATIONS

Office Action for CN Patent Application No. 2018800132331, dated Aug. 11, 2021, 9 pages of Office Action and 9 pages of English Translation.

* cited by examiner

: large bowel

: large bowel

MEDICAL ARM SYSTEM, CONTROL DEVICE, AND CONTROL METHOD

CROSS REFERENCE TO RELATED APPLICATIONS

This application is a U.S. National Phase of International Patent Application No. PCT/JP2018/005465 filed on Feb. 16, 2018, which claims priority benefit of Japanese Patent Application No. JP 2017-036843 filed in the Japan Patent Office on Feb. 28, 2017 and also claims priority benefit of Japanese Patent Application No. JP 2017-036842 filed in the Japan Patent Office on Feb. 28, 2017. Each of the above-referenced applications is hereby incorporated herein by reference in its entirety.

TECHNICAL FIELD

The present disclosure relates to a medical arm system, a control device, and a control method.

BACKGROUND ART

In recent years, technological developments for medical equipment have been actively conducted. For example, the following Patent Document 1 discloses a technology that relates to a medical manipulator in a remote operation-type surgery system and a method of controlling the same, and particularly a technology to support minimally invasive surgery such as laparoscopic surgery and laparo-thoraco-scopic surgery, which are conducted by inserting a medical instrument such as an endoscope and forceps into a human body.

CITATION LIST

Patent Document

Patent Document 1: International Publication No. 2014/199413

SUMMARY OF THE INVENTION

Problems to be Solved by the Invention

However, only a little time has passed since the development of the technology disclosed in the above-described Patent Document 1 or the like, and it is difficult to say that sufficient proposals have been made from various viewpoints. For example, to secure safety during surgery is one of the viewpoints from which a sufficient proposal has not been made.

Therefore, the present disclosure proposes a mechanism capable of securing both convenience and safety in regard to surgery performed by inserting an endoscope into a human body.

Solutions to Problems

According to the present disclosure, proposed is a medical arm system including: a multi-joint arm which has a plurality of links connected by joints and a distal end to which an endoscope is connectable; and a control unit which sets a virtual plane in a body cavity of a patient and controls the multi-joint arm so as to constrain a predetermined point of the endoscope in the body cavity on the virtual plane.

Furthermore, according to the present disclosure, proposed is a control device including a control unit which sets a virtual plane in a body cavity of a patient and controls a multi-joint arm, which has a plurality of links connected by joints and a distal end to which an endoscope is connectable, so as to constrain a predetermined point of the endoscope in the body cavity on the virtual plane.

Furthermore, according to the present disclosure, proposed is a control method executed by a processor, the control method including: setting a virtual plane in a body cavity of a patient; and controlling a multi-joint arm, which has a plurality of links connected by joints and a distal end to which an endoscope is connectable, so as to constrain a predetermined point of the endoscope in the body cavity on the virtual plane.

Effects of the Invention

As described above, the mechanism capable of securing both the convenience and the security in regard to the surgery performed by inserting the endoscope into the human body is provided according to the present disclosure. Note that the above-described effect is not necessarily limited, and any effect illustrated in the present specification or other effects that can be grasped from the present specification may be exhibited in addition to the above-described effect or instead of the above-described effect.

MODE FOR CARRYING OUT THE INVENTION

Hereinafter, preferred embodiments of the present disclosure will be described in detail with reference to the accompanying drawings. Note that components having substantially the same functional configuration in the present specification and the drawings will be denoted by the same reference sign, and the redundant description thereof will be omitted.

Note that a description will be given in the following order.

1. Basic Configuration
1.1. Configuration Example of Endoscopic Surgery System
1.2. Specific Configuration Example of Medical Support Arm Device
1.3. Configuration Example of Control Device
2. First Embodiment
2.1. Overview
2.2. Details
3. Second Embodiment
3.1. Overview
3.2. Details
4. Summary 1. Basic Configuration First, a basic configuration of an endoscopic surgery system according to an embodiment of the present disclosure will be described with reference to FIGS. 1 to 4.

1.1. Configuration Example of Endoscopic Surgery System

Figure 1:
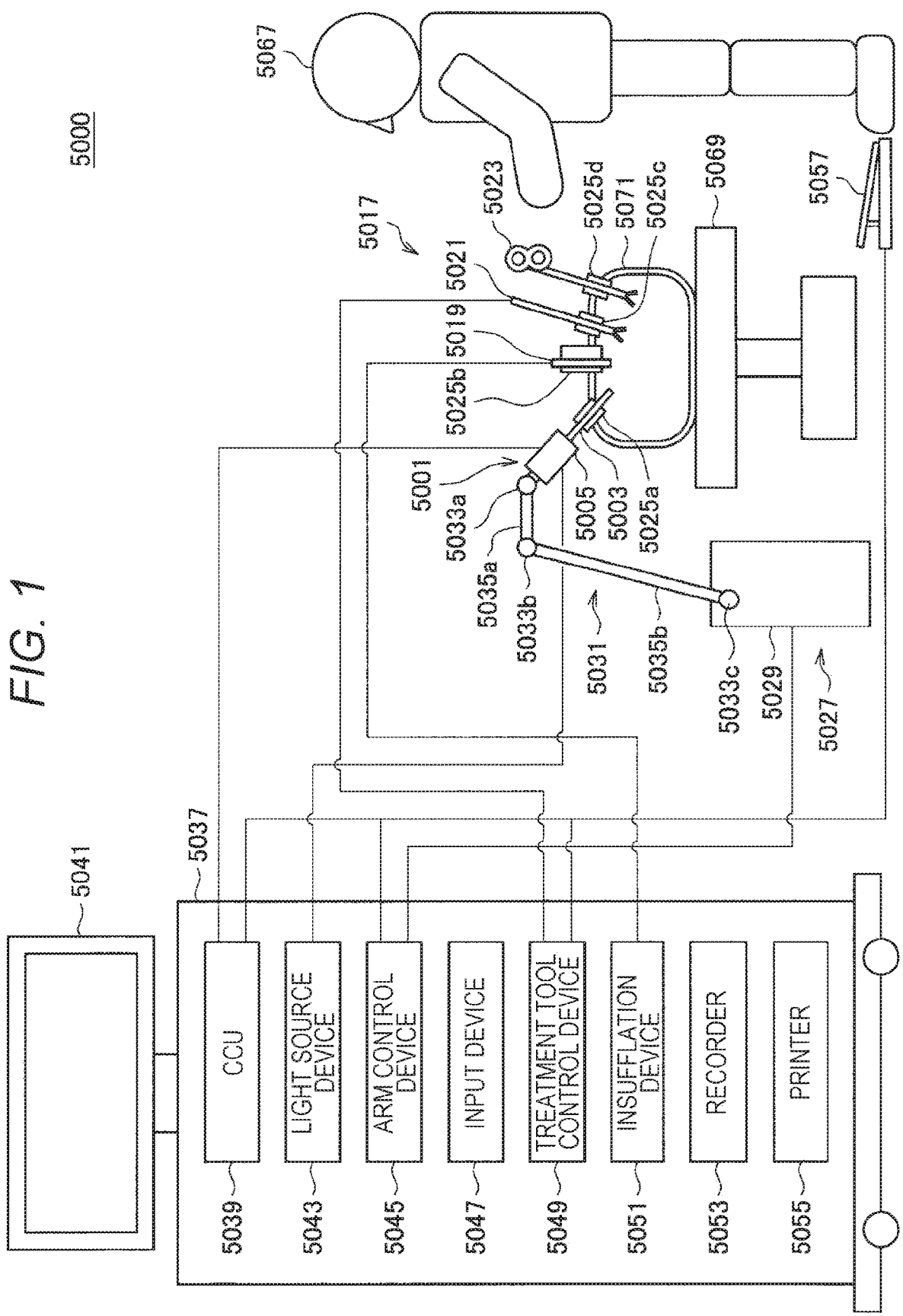
FIG. 1 is a diagram illustrating an example of a schematic configuration of an endoscopic surgery system to which a medical support arm device according to the present disclosure can be applied.

FIG. 1 is a diagram illustrating an example of a schematic configuration of an endoscopic surgery system 5000 to which the technology according to the present disclosure can be applied. FIG. 1 illustrates a state where an operator (doctor) 5067 is conducting surgery to a patient 5071 on a patient bed 5069 using the endoscopic surgery system 5000. As illustrated, the endoscopic surgery system 5000 is constituted by an endoscope 5001, other surgical tools 5017, and a support arm device 5027 supporting the endoscope 5001, and a cart 5037 on which various devices for endoscopic surgery are mounted.

In the endoscopic surgery, the abdominal wall is punctured with a plurality of tubular hole-opening instruments called trocars 5025a to 5025d instead of cutting the abdominal wall to open the abdomen. Then, a lens barrel 5003 of the endoscope 5001 and the other surgical tools 5017 are inserted into a body cavity of the patient 5071 through the trocars 5025a to 5025d. In the illustrated example, as the other surgical tools 5017, an insufflation tube 5019, an energy treatment tool 5021, and forceps 5023 are inserted into the body cavity of the patient 5071. Furthermore, the energy treatment tool 5021 is a treatment tool that performs incision and peeling of a tissue, sealing of a blood vessel, or the like using high-frequency current or ultrasonic vibration. However, the illustrated surgical tool 5017 is merely an example, and various surgical tools generally used in endoscopic surgery, for example, tweezers, a retractor, and the like may be used as the surgical tool 5017.

An image of an operation site in the body cavity of the patient 5071 captured by the endoscope 5001 is displayed on a display device 5041. The operator 5067 performs treatment, for example, to excise an affected site using the energy treatment tool 5021 or the forceps 5023 while viewing the image of the operation site displayed by the display device 5041 in real time. Note that the insufflation tube 5019, the energy treatment tool 5021, and the forceps 5023 are supported by the operator 5067, an assistant, or the like during surgery although not illustrated.

(Support Arm Device)

The support arm device 5027 includes an arm unit 5031 extending from a base unit 5029. In the illustrated example, the arm unit 5031 is a multi-joint arm constituted by joints 5033a, 5033b, and 5033c and links 5035a and 5035b, and is driven by control from an arm control device 5045. The arm unit 5031 has a distal end to which the endoscope 5001 can be connected. The endoscope 5001 is supported by the arm unit 5031, and a position and a posture thereof are controlled. With the configuration, it is possible to realize stable fixing of the position of the endoscope 5001.

(Endoscope)

The endoscope 5001 is constituted by the lens barrel 5003 having a region of a predetermined length from a distal end that is inserted into the body cavity of the patient 5071, and a camera head 5005 connected to a proximal end of the lens barrel 5003. Although the endoscope 5001 configured as a so-called rigid scope having the rigid lens barrel 5003 is illustrated in the illustrated example, the endoscope 5001 may be configured as a so-called flexible scope having the flexible lens barrel 5003.

An opening portion into which an objective lens is fitted is provided at the distal end of the lens barrel 5003. A light source device 5043 is connected to the endoscope 5001, and light generated by the light source device 5043 is guided to the distal end of the lens barrel by a light guide extended inside the lens barrel 5003 and is emitted toward an observation object in the body cavity of the patient 5071 through the objective lens. Note that the endoscope 5001 may be a forward-viewing scope, an oblique-viewing scope, or a side-viewing scope.

An optical system and an imaging element are provided inside the camera head 5005, and reflected light (observation light) from the observation object is collected on the imaging element by the optical system. The observation light is photoelectrically converted by the imaging element, and an electric signal corresponding to the observation light, in other words, an image signal corresponding to an observation image is generated. The image signal is transmitted as RAW data to a camera control unit (CCU) 5039. Note that the camera head 5005 is equipped with a function of adjusting magnification and a focal length by properly driving the optical system.

Note that a plurality of imaging elements may be provided in the camera head 5005, for example, in order to cope with stereoscopic viewing (3D display) or the like. In this case, a plurality of relay optical systems is provided inside the lens barrel 5003 in order to guide the observation light to each of the plurality of imaging elements.

(Various Devices Equipped in Cart)

The CCU 5039 is configured using a central processing unit (CPU), a graphics processing unit (GPU), or the like, and integrally controls operations of the endoscope 5001 and the display device 5041. Specifically, the CCU 5039 performs various types of image processing, for example, development processing (demosaicing processing) or the like on an image signal received from the camera head 5005 to display an image based on the image signal. The CCU 5039 provides the image signal subjected to the image processing to the display device 5041. Furthermore, the CCU 5039 transmits a control signal to the camera head 5005 and controls drive of the camera head 5005. The control signal may include information regarding imaging conditions such as magnification and a focal length.

The display device 5041 displays an image based on the image signal subjected to image processing by the CCU 5039 under the control of the CCU 5039. In a case where the endoscope 5001 is an endoscope compatible with high-resolution capturing, for example, 4K (the number of horizontal pixels of 3840×the number of vertical pixels of 2160), 8K (the number of horizontal pixels of 7680×the number of vertical pixels of 4320) or the like, and/or in a case of an endoscope compatible with 3D display, a device capable of high-resolution display and/or a device capable of 3D display can be used as the display device 5041 to be compatible with the above endoscopes, respectively. In the case of the endoscope compatible with the high-resolution capturing such as 4K and 8K, a more immersive feeling can be obtained by using the display device 5041 having a size of 55 inches or more. Furthermore, a plurality of the display devices 5041 having different resolutions and sizes may be provided in accordance with an application.

The light source device 5043 is configured using a light source such as a light emitting diode (LED), for example, and supplies irradiation light at the time of capturing an operation site to the endoscope 5001.

The arm control device 5045 is configured using a processor, for example, a CPU or the like, and operates according to a predetermined program to control the drive of the arm unit 5031 of the support arm device 5027 according to a predetermined control method.

The input device 5047 is an input interface with respect to the endoscopic surgery system 5000. A user can input various types of information and instructions to the endoscopic surgery system 5000 via the input device 5047. For example, the user inputs various types of information regarding surgery, such as information regarding a patient's body and information regarding surgical operation technology via the input device 5047. Furthermore, for example, the user inputs an instruction to drive the arm unit 5031, an instruction to change an imaging condition (a type of irradiated light, magnification, a focal length, or the like) using the endoscope 5001, an instruction to drive the energy treatment tool 5021, and the like via the input device 5047.

The type of the input device 5047 is not limited, and the input device 5047 may be various known input devices. For example, a mouse, a keyboard, a touch panel, a switch, a foot switch 5057 and/or a lever can be applied as the input device 5047. In a case where a touch panel is used as the input device 5047, the touch panel may be provided on a display surface of the display device 5041.

Alternatively, the input device 5047 is, for example, a device to be mounted by the user, such as a glasses-type wearable device and a head-mounted display (HMD), and various inputs are performed in accordance with a gesture or a line of sight of the user detected by these devices. Furthermore, the input device 5047 includes a camera capable of detecting user's motion, and various inputs are performed in accordance with a gesture or a line of sight of the user detected from an image captured by the camera. Moreover, the input device 5047 includes a microphone capable of collecting user's voice, and various inputs are performed using the voice through the microphone. In this manner, the input device 5047 is configured to be capable of inputting various types of information in a non-contact manner, and particularly, the user (for example, the operator 5067) belonging to a clean area can operate equipment belonging to an unclean area in a non-contact manner. Furthermore, the user can operate the equipment without releasing his/her hand from the possessed surgical tool, and thus, the convenience of the user is improved.

The treatment tool control device 5049 controls the drive of the energy treatment tool 5021 for cauterization of a tissue, an incision, sealing of a blood vessel, or the like. An insufflation device 5051 sends a gas into a body cavity through the insufflation tube 5019 in order t to inflate the body cavity of the patient 5071 for the purpose of securing a visual field by the endoscope 5001 and securing a working space for the operator. A recorder 5053 is a device capable of recording various types of information regarding surgery. A printer 5055 is a device capable of printing various types of information regarding surgery in various formats such as text, an image, and a graph.

Hereinafter, a particularly characteristic configuration in the endoscopic surgery system 5000 will be described in more detail.

(Support Arm Device)

The support arm device 5027 includes the base unit 5029 as a base and the arm unit 5031 extending from the base unit 5029. Although the arm unit 5031 is constituted by the plurality of joints 5033a, 5033b, and 5033c, and the plurality of links 5035a and 5035b connected by the joint 5033b in the illustrated example, FIG. 1 illustrates the configuration of the arm unit 5031 in a simplified manner for the sake of simplicity. Actually, each shape, the number, and the arrangement of the joints 5033a to 5033c and the links 5035a and 5035b, a direction of a rotation axis of each of the joints 5033a to 5033c, and the like are appropriately set such that the arm unit 5031 has a desired degree of freedom. For example, the arm unit 5031 can be preferably configured to have the degree of freedom equal to or greater than six degrees of freedom. With the configuration, the endoscope 5001 can be freely moved within a movable range of the arm unit 5031, and thus, it is possible to insert the lens barrel 5003 of the endoscope 5001 into the body cavity of the patient 5071 from a desired direction.

Actuators are provided in the joints 5033a to 5033c, and the joints 5033a to 5033c are configured to be rotatable about a predetermined rotation axis by the drive of the actuators. As the drive of the actuator is controlled by the arm control device 5045, each rotation angle of the joints 5033a to 5033c is controlled, and the drive of the arm unit 5031 is controlled. With the configuration, the control of the position and the posture of the endoscope 5001 can be realized. At this time, the arm control device 5045 can control the drive of the arm unit 5031 by various known control methods such as force control or position control.

For example, the position and posture of the endoscope 5001 may be controlled as the operator 5067 appropriately performs an operation input via the input device 5047 (including the foot switch 5057) and the drive of the arm unit 5031 is appropriately controlled by the arm control device 5045 according to the operation input. Through such control, the endoscope 5001 at the distal end of the arm unit 5031 can be moved from an arbitrary position to an arbitrary position, and then, fixedly supported at a position after the movement. Note that the arm unit 5031 may be operated in a so-called master-slave manner. In this case, the arm unit 5031 can be remotely operated by the user via the input device 5047 installed at a place distant from an operating room.

Furthermore, in a case where the force control is applied, the arm control device 5045 may receive an external force from the user and perform so-called power assist control to drive the actuators of the joints 5033a to 5033c such that the arm unit 5031 moves smoothly according to the external force. With the configuration, when the user moves the arm unit 5031 while directly touching the arm unit 5031, the arm unit 5031 can be moved with a relatively light force. Therefore, it is possible to more intuitively move the endoscope 5001 with a simpler operation, and it is possible to improve the convenience of the user.

Here, the endoscope 5001 has been generally supported by a doctor called a scopist in endoscopic surgery. In regard to this, it becomes possible to more reliably fix the position of the endoscope 5001 without human hands by using the support arm device 5027, and thus, it is possible to stably obtain an image of an operation site and to smoothly perform the surgery.

Note that the arm control device 5045 is not necessarily provided in the cart 5037. Furthermore, the arm control device 5045 is not necessarily one device. For example, the arm control device 5045 may be provided at each of joints 5033a to 5033c of the arm unit 5031 of the support arm device 5027, or the drive control of the arm unit 5031 may be realized by the plurality of arm control devices 5045 cooperating with each other.

(Light Source Device)

The light source device 5043 supplies irradiation light at the time of capturing an operation site to the endoscope 5001. The light source device 5043 is configured using, for example, a white light source constituted by an LED, a laser light source, or a combination thereof. At this time, in a case where the white light source is constituted by a combination of RGB laser light sources, the output intensity and output timing of each color (each wavelength) can be controlled with high precision, and thus, it is possible to adjust white balance of a captured image in the light source device 5043. Furthermore, in this case, it is also possible to capture an image corresponding to each of RGB in a time-division manner by irradiating an observation object with laser light from each of the RGB laser light sources in a time-division manner and controlling the drive of the imaging element of the camera head 5005 in synchronization with an irradiation timing. According to this method, a color image can be obtained without providing a color filter in the imaging element.

Furthermore, the drive of the light source device 5043 may be controlled so as to change the intensity of light to be output every predetermined time. The drive of the imaging element of the camera head 5005 is controlled in synchronization with a timing of the change of the light intensity to acquire images in a time-division manner, and a so-called high dynamic range image without so-called crushed blacks and blown-out whites can be generated by combining the images.

Furthermore, the light source device 5043 may be configured to be capable of supplying light in a predetermined wavelength band which is compatible with special light observation. In the special light observation, for example, the wavelength dependency of light absorption in a body tissue is utilized, and light is emitted in a narrow band as compared to irradiation light during normal observation (in other words, white light), thereby performing so-called narrow band imaging (NBI) in which a predetermined tissue, such as a blood vessel in a superficial portion of a mucous membrane, is captured at a high contrast. Alternatively, fluorescent observation that obtains an image with fluorescent light generated by emitting excitation light may also be performed in the special light observation. In the fluorescence observation, it is possible to irradiate a body tissue with excitation light and observe fluorescent light from the body tissue (autofluorescence observation), to locally inject a reagent such as indocyanine green (ICG) into a body tissue and also irradiate the body tissue with excitation light corresponding to a fluorescence wavelength of the reagent to obtain a fluorescent image, or the like. The light source device 5043 can be configured to be capable of supplying narrow-band light and/or excitation light corresponding to such special light observation.

(Camera Head and CCU)

Figure 2:
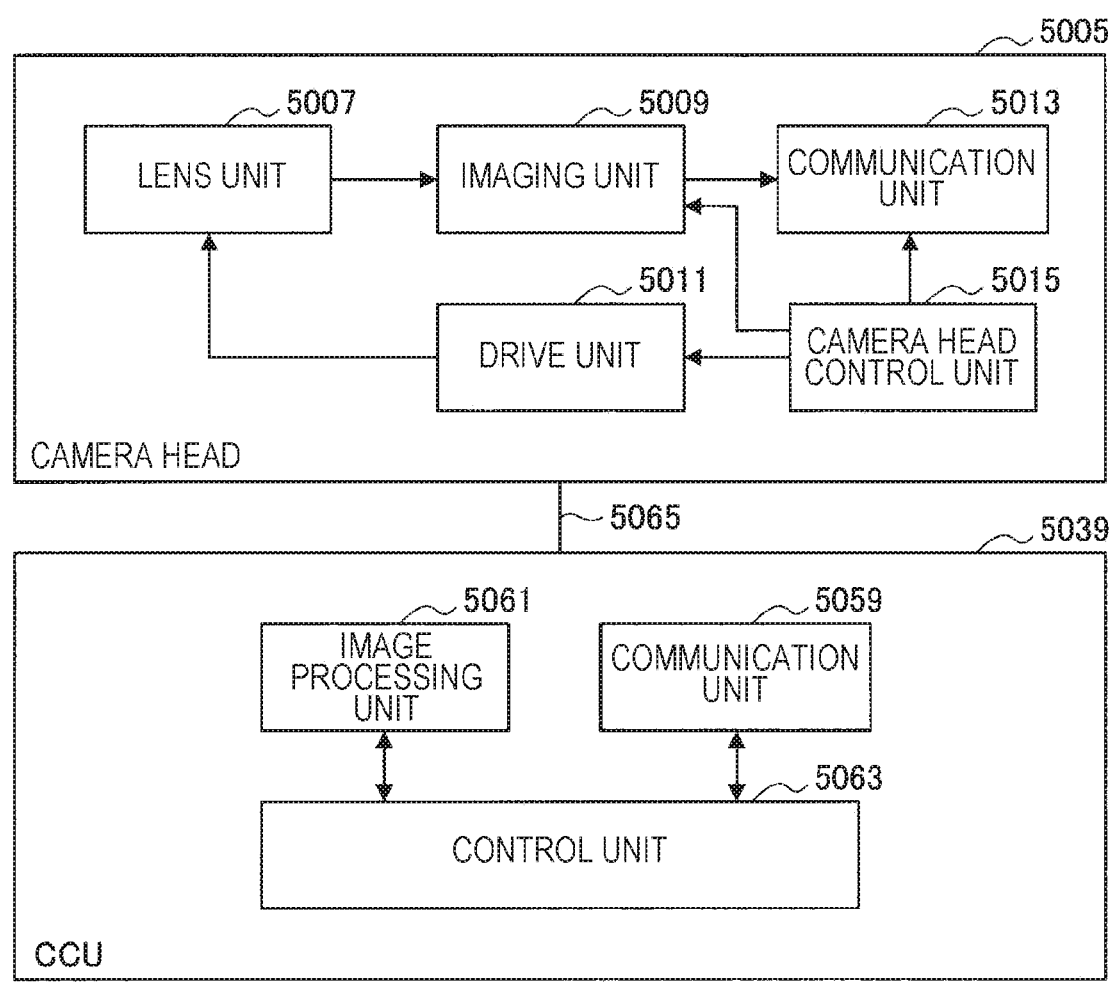
FIG. 2 is a block diagram illustrating an example of functional configurations of a camera head and a CCU illustrated in FIG. 1.

Functions of the camera head 5005 and the CCU 5039 of the endoscope 5001 will be described in more detail with reference to FIG. 2. FIG. 2 is a block diagram illustrating an example of functional configurations of the camera head 5005 and the CCU 5039 illustrated in FIG. 1.

The camera head 5005 has a lens unit 5007, an imaging unit 5009, a drive unit 5011, a communication unit 5013, and a camera head control unit 5015 as functions thereof with reference to FIG. 2. Furthermore, the CCU 5039 has a communication unit 5059, an image processing unit 5061, and a control unit 5063 as functions thereof. The camera head 5005 and the CCU 5039 are connected to be capable of bi-directional communication via a transmission cable 5065.

First, the functional configuration of the camera head 5005 will be described. The lens unit 5007 is an optical system provided at a connection portion with the lens barrel 5003. Observation light taken in from the distal end of the lens barrel 5003 is guided to the camera head 5005 and is incident onto the lens unit 5007. The lens unit 5007 is configured by combining a plurality of lenses including a zoom lens and a focus lens. Optical characteristics of the lens unit 5007 are adjusted such that observation light is collected on a light receiving surface of an imaging element of the imaging unit 5009. Furthermore, the zoom lens and the focus lens are configured such that positions on the optical axis thereof can be moved for adjustment of magnification and a focal length of a captured image.

The imaging unit 5009 is constituted by the imaging element, and is arranged at the subsequent stage of the lens unit 5007. The observation light having passed through the lens unit 5007 is collected on the light receiving surface of the imaging element, and an image signal corresponding to the observation image is generated by photoelectric conversion. The image signal generated by the imaging unit 5009 is provided to the communication unit 5013.

As the imaging element constituting the imaging unit 5009, for example, a complementary metal oxide semiconductor (CMOS) type image sensor that is capable of color capturing having the Bayer arrangement can be used. Note that, for example, an imaging element capable of being compatible with capturing of a high-resolution image of 4K or more may be used as the imaging element. Since the high-resolution image of an operation site can be obtained, the operator 5067 can grasp a situation of the operation site in more detail and can proceed surgery more smoothly.

Furthermore, the imaging element constituting the imaging unit 5009 is configured to have a pair of imaging elements to acquire image signals for a right eye and a left eye, respectively, compatible with 3D display. As the 3D display is performed, the operator 5067 can more accurately grasp a depth of a living tissue in the operation site. Note that a plurality of the lens units 5007 is provided to correspond to the respective imaging elements in a case where the imaging unit 5009 is configured in a multi-plate type.

Furthermore, the imaging unit 5009 is not necessarily provided in the camera head 5005. For example, the imaging unit 5009 may be provided inside the lens barrel 5003 just behind an objective lens.

The drive unit 5011 is configured using an actuator, and the zoom lens and the focus lens of the lens unit 5007 are moved along the optical axis by a predetermined distance under the control of the camera head control unit 5015. With the movement, the magnification and the focal length of the image captured by the imaging unit 5009 can be appropriately adjusted.

The communication unit 5013 is configured using a communication device to transmit and receive various types of information to and from the CCU 5039. The communication unit 5013 transmits an image signal obtained from the imaging unit 5009 as RAW data to the CCU 5039 via the transmission cable 5065. In this case, it is preferable that the image signal be transmitted by optical communication in order to display the captured image of the operation site with low latency. During surgery, the operator 5067 performs the surgery while observing a state of the affected site through the captured image, and thus, it is required to display a moving image of the operation site in real time as much as possible in order for a safer and more reliable surgery. In the case where the optical communication is performed, a photoelectric conversion module that converts an electric signal into an optical signal is provided in the communication unit 5013. The image signal is converted into the optical signal by the photoelectric conversion module, and then, is transmitted to the CCU 5039 via the transmission cable 5065.

Furthermore, the communication unit 5013 receives a control signal to control the drive of the camera head 5005 from the CCU 5039. The control signal includes information regarding imaging conditions such as information to designate a frame rate of a captured image, information to designate an exposure value at the time of imaging, and/or information to designate magnification and a focal length of a captured image, for example. The communication unit 5013 provides the received control signal to the camera head control unit 5015. Note that a control signal from the CCU 5039 may also be transmitted by optical communication. In this case, the communication unit 5013 is provided with a photoelectric conversion module that converts an optical signal into an electric signal, and the control signal is converted into the electrical signal by the photoelectric conversion module, and then, is provided to the camera head control unit 5015.

Note that the imaging conditions such as the above-described frame rate, exposure value, magnification, and focal length are automatically set by the control unit 5063 of the CCU 5039 on the basis of the acquired image signal. That is, the endoscope 5001 is equipped with so-called auto exposure (AE) function, auto focus (AF) function, and auto white balance (AWB) function.

The camera head control unit 5015 controls the drive of the camera head 5005 on the basis of the control signal from the CCU 5039 received via the communication unit 5013. For example, the camera head control unit 5015 controls the drive of the imaging element of the imaging unit 5009 on the basis of the information to designate the frame rate of the captured image and/or the information to designate the exposure at the time of imaging. Furthermore, for example, the camera head control unit 5015 appropriately moves the zoom lens and the focus lens of the lens unit 5007 via the drive unit 5011 on the basis of the information to designate the magnification and the focal length of the captured image. Moreover, the camera head control unit 5015 may have a function of storing information to identify the lens barrel 5003 and the camera head 5005.

Note that the camera head 5005 can be made resistant to autoclave sterilization processing by arranging the configurations of the lens unit 5007, the imaging unit 5009, and the like in a sealed structure with high airtightness and waterproofness.

Next, the functional configuration of the CCU 5039 will be described. The communication unit 5059 is configured using a communication device to transmit and receive various types of information to and from the camera head 5005. The communication unit 5059 receives an image signal transmitted from the camera head 5005 via the transmission cable 5065. In this case, the image signal can be suitably transmitted by optical communication as described above. In this case, the communication unit 5059 is provided with a photoelectric conversion module that converts an optical signal into an electric signal to be compatible with the optical communication. The communication unit 5059 provides the image signal that has been converted into the electric signal to the image processing unit 5061.

Furthermore, the communication unit 5059 transmits a control signal to control the drive of the camera head 5005 to the camera head 5005. The control signal may also be transmitted by optical communication.

The image processing unit 5061 performs various types of image processing on the image signal which is RAW data transmitted from the camera head 5005. For examples, the image processing includes various types of known signal processing such as development processing, image quality improvement processing (band enhancement processing, super-resolution processing, noise reduction (NR) processing and/or camera shake correction processing, for example), and/or enlargement processing (electronic zoom processing). Furthermore, the image processing unit 5061 performs the detection processing on an image signal for performing AE, AF, and AWB.

The image processing unit 5061 is configured using a processor such as a CPU and a GPU, and the above-described image processing and detection processing can be performed when the processor operates according to a predetermined program. Note that, in a case where the image processing unit 5061 is constituted by a plurality of GPUs, the image processing unit 5061 appropriately divides information regarding the image signal and performs the image processing in parallel by the plurality of GPUs.

The control unit 5063 performs various types of control regarding imaging of an operation site using the endoscope 5001 and display of such a captured image. For example, the control unit 5063 generates a control signal to control the drive of the camera head 5005. At this time, in a case where an imaging condition is input by a user, the control unit 5063 generates the control signal on the basis of the input by the user. Alternatively, in a case where the endoscope 5001 is equipped with the AE function, the AF function, and the AWB function, the control unit 5063 appropriately calculates optimal exposure value, focal length, and white balance to generate the control signal in accordance with a result of the detection processing by the image processing unit 5061.

Furthermore, the control unit 5063 causes the display device 5041 to display the image of the operation site on the basis of the image signal subjected to the image processing by the image processing unit 5061. At this time, the control unit 5063 recognizes various objects in the image of the operation site using various image recognition technologies. For example, the control unit 5063 detects a shape of an edge, a color, and the like of an object included in the operation site image, and thus, can recognize a surgical tool such as forceps, a specific living body part, bleeding, mist at the time of using the energy treatment tool 5021, and the like. When the display device 5041 is caused to display the image of the operation site, the control unit 5063 causes various types of surgical support information to be superimposed and displayed on the image of the operation site using such a recognition result. Since the surgical support information is superimposed and displayed, and presented to the operator 5067, it is possible to proceed the surgery more safely and reliably.

The transmission cable 5065 connecting the camera head 5005 and the CCU 5039 is an electric signal cable compatible with communication of an electric signal, an optical fiber compatible with optical communication, or a composite cable thereof.

Here, communication is performed in a wired manner using the transmission cable 5065 in the illustrated example, but the communication between the camera head 5005 and the CCU 5039 may be performed in a wireless manner. In the case where the communication between the two is performed in a wireless manner, it is not necessary to lay the transmission cable 5065 in the operating room, and thus, a situation in which movement of a medical staff is hindered by the transmission cable 5065 in the operating room can be resolved.

An example of the endoscopic surgery system 5000 to which the technology according to the present disclosure can be applied has been described as above. Note that the endoscopic surgery system 5000 has been described as an example here, but a system to which the technology according to the present disclosure can be applied is not limited to such an example. For example, the technology according to the present disclosure may be applied to a flexible endoscope system for inspection or a microscopic surgery system.

1.2. Specific Configuration Example of Medical Support Arm Device

Next, a specific configuration example of a medical support arm device according to an embodiment of the present disclosure will be described in detail. Although the support arm device described hereinafter is an example configured as a support arm device that supports an endoscope at a distal end of an arm unit, the present embodiment is not limited to the example.

Figure 3:
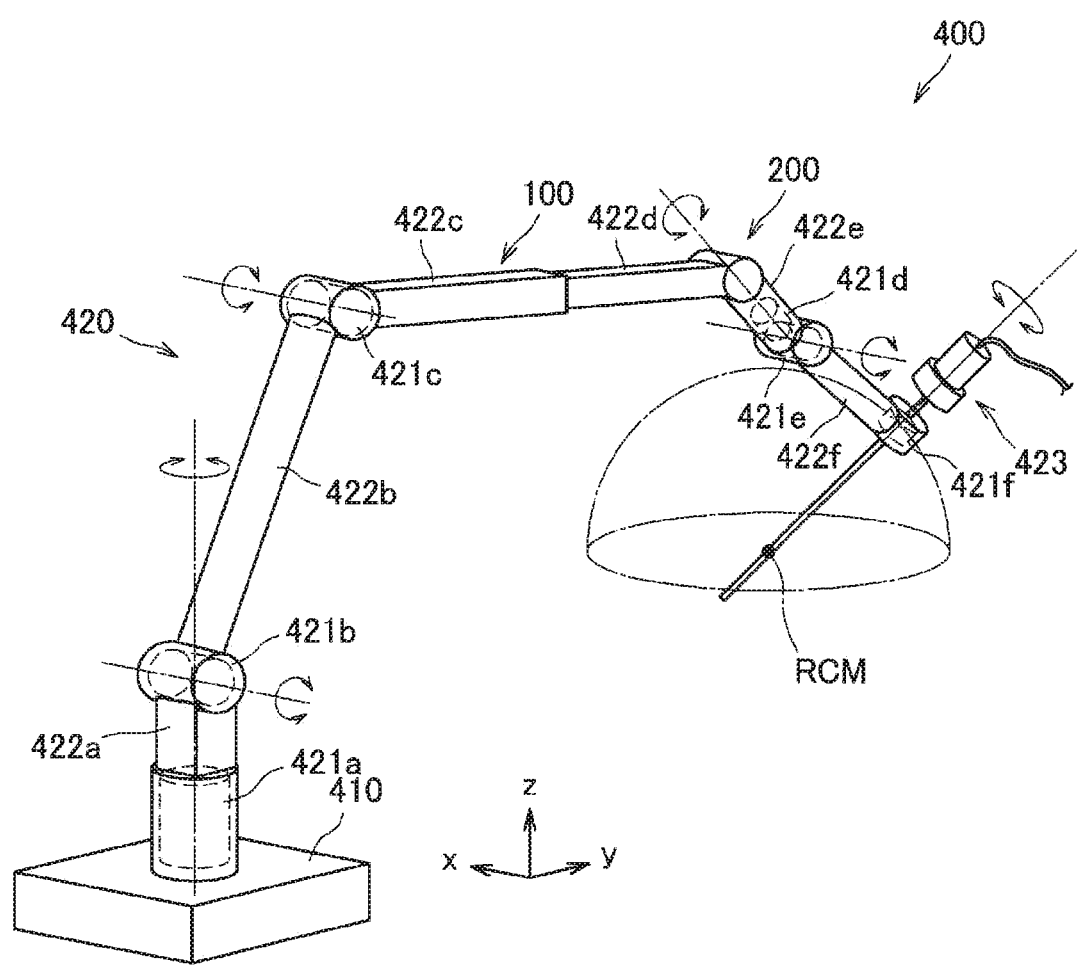
FIG. 3 is a perspective view illustrating a configuration example of a medical support arm device according to an embodiment of the present disclosure.

First, a schematic configuration of a support arm device 400 according to the present embodiment will be described with reference to FIG. 3. FIG. 3 is a schematic view illustrating an appearance of the support arm device 400 according to the present embodiment.

The support arm device 400 according to the present embodiment includes a base unit 410 and an arm unit 420. The base unit 410 is a base of the support arm device 400, and the arm unit 420 is extended from the base unit 410. Furthermore, a control unit that integrally controls the support arm device 400 may be provided in the base unit 410 although not illustrated in FIG. 3, and the drive of the arm unit 420 may be controlled by the control unit. The control unit is constituted by various signal processing circuits, for example, a CPU, a DSP, and the like.

The arm unit 420 includes a plurality of active joints 421*a* to 421*f*, a plurality of links 422*a* to 422*f*, and an endoscope device 423 as a distal unit provided at a distal end of the arm unit 420.

The links 422*a* to 422*f* are substantially rod-shaped members. One end of the link 422*a* is connected to the base unit 410 via the active joint 421*a*, and the other end of the link 422*a* is connected to one end of the link 422*b* via the active joint 421*b*. Moreover, the other end of the link 422*b* is connected to one end of the link 422*c* via the active joint 421*c*. The other end of the link 422*c* is connected to the link 422*d* via a passive slide mechanism 100. Moreover, the other end of the link 422*d* is connected to one end of the link 422*e* via a passive joint 200. The other end of the link 422*e* is connected to one end of the link 422*f* via the active joints 421*d* and 421*e*. The endoscope device 423 is connected to the distal end of the arm unit 420, in other words, the other end of the link 422*f* via the active joint 421*f*. In this manner, ends of the plurality of links 422*a* to 422*f* are connected to each other by the active joints 421*a* to 421*f*, the passive slide mechanism 100, and the passive joint 200 using the base unit 410 as a fulcrum so that an arm shape extended from the base unit 410 is configured.

A position and a posture of the endoscope device 423 are controlled by driving and controlling actuators provided in the active joints 421*a* to 421*f* of the arm unit 420. In the present embodiment, the endoscope device 423 causes a distal end thereof to enter patient's body cavity, which is a treatment site, and captures a partial region of the treatment site. However, the distal unit provided at the distal end of the arm unit 420 is not limited to the endoscope device 423, and various medical instruments may be connected to the distal end of the arm unit 420 as the distal unit. In this manner, the support arm device 400 according to the present embodiment is configured as a medical support arm device provided with a medical instrument.

Here, the support arm device 400 will be described by defining coordinate axes as illustrated in FIG. 3 as follows. Furthermore, a vertical direction, a longitudinal direction, and a horizontal direction are defined according to the coordinate axes. In other words, a vertical direction with respect to the base unit 410 installed on the floor surface is defined as a z-axis direction and the vertical direction. Furthermore, a direction orthogonal to the z axis, the direction in which the arm unit 420 is extended from the base unit 410 (in other words, a direction in which the endoscope device 423 is positioned with respect to the base unit 410)

is defined as a y-axis direction and the longitudinal direction. Moreover, a direction orthogonal to the y-axis and z-axis is defined as an x-axis direction and the horizontal direction.

The active joints 421a to 421f connect the links to each other to be rotatable. The active joints 421a to 421f have the actuators, and have each rotation mechanism that is driven to rotate about a predetermined rotation axis by drive of the actuator. As the rotational drive of each of the active joints 421a to 421f is controlled, it is possible to control the drive of the arm unit 420, for example, to extend or contract (fold) the arm unit 420. Here, each drive of the active joints 421a to 421f can be controlled by, for example, known whole body cooperative control and ideal joint control. Since the active joints 421a to 421f have the rotation mechanisms as described above, in the following description, the drive control of the active joints 421a to 421f specifically means that rotation angles and/or generation torques (torques generated by the active joints 421a to 421f) of the active joints 421a to 421f are controlled.

The passive slide mechanism 100 is an aspect of a passive form change mechanism, and connects the link 422c and the link 422d to each other to be movable forward and rearward along a predetermined direction. For example, the passive slide mechanism 100 may connect the link 422c and the link 422d to each other to be linearly movable. However, the forward and rearward movement between the link 422c and the link 422d is not limited to the linear movement, and may be forward and rearward movement in a direction to form an arc. The passive slide mechanism 100 is operated to move forward and rearward by, for example, a user, and a distance between the active joint 421c at one end side of the link 422c and the passive joint 200 is variable. With the configuration, the whole form of the arm unit 420 can be changed. Details of a configuration of the passive slide mechanism 100 will be described later.

The passive joint 200 is an aspect of the passive form change mechanism, and connects the link 422d and the link 422e to each other to be rotatable. The passive joint 200 is operated to rotate by, for example, the user, and an angle formed between the link 422d and the link 422e is variable. With the configuration, the whole form of the arm unit 420 can be changed. Details of a configuration of the passive joint 200 will be described later.

Note that the "posture of the arm unit" refers to a state of the arm unit that can be changed by the drive control of the actuators provided in the active joints 421a to 421f by the control unit in a state where a distance between the active joints adjacent to each other with one or a plurality of links interposed therebetween is constant in the present specification. Furthermore, the "form of the arm unit" refers to a state of the arm unit that can be changed as a distance between the active joints adjacent to each other with a link interposed therebetween or an angle formed between links connecting the adjacent active joints is changed along with the operation of the passive form change mechanism.

The support arm device 400 according to the present embodiment has the six active joints 421a to 421f, and six degrees of freedom are realized regarding the drive of the arm unit 420. That is, the passive slide mechanism 100 and the passive joint 200 are not objects to be subjected to the drive control using the control unit while the drive control of the support arm device 400 is realized by the drive control of the six active joints 421a to 421f using the control unit.

Specifically, as illustrated in FIG. 3 the active joints 421a, 421d, and 421f are provided so as to have each long axis direction of the connected links 422a and 422e and a capturing direction of the connected endoscope device 423 as a rotational axis direction. The active joints 421b, 421c, and 421e are provided so as to have the x-axis direction, which is a direction in which a connection angle of each of the connected links 422a to 422c, 422e, and 422f and the endoscope device 423 is changed within a y-z plane (a plane defined by the y axis and the z axis), as a rotation axis direction. In this manner, in the present embodiment, the active joints 421a, 421d, and 421f have a function of performing so-called yawing, and the active joints 421b, 421c, and 421e have a function of performing so-called pitching.

Since the six degrees of freedom are realized with respect to the drive of the arm unit 420 in the support arm device 400 according to the present embodiment with such a configuration of the arm unit 420, the endoscope device 423 can be freely moved within a movable range of the arm unit 420. FIG. 3 illustrates a hemisphere as an example of the movable range of the endoscope device 423. Assuming that a central point RCM (remote center of motion) of the hemisphere is a capturing center of a treatment site captured by the endoscope device 423, it is possible to capture the treatment site from various angles by moving the endoscope device 423 on a spherical surface of the hemisphere in a state where the capturing center of the endoscope device 423 is fixed at the center point of the hemisphere.

1.3. Configuration Example of Control Device

The configuration of the support arm device 400 according to the present embodiment has been described so far. Hereinafter, a description will be given regarding a configuration of a control device for the drive control of the arm unit 420 in the support arm device 400 according to the present embodiment, in other words, the control of the rotational drive of an actuator 430 provided in the active joints 421a to 421f.

Figure 4:
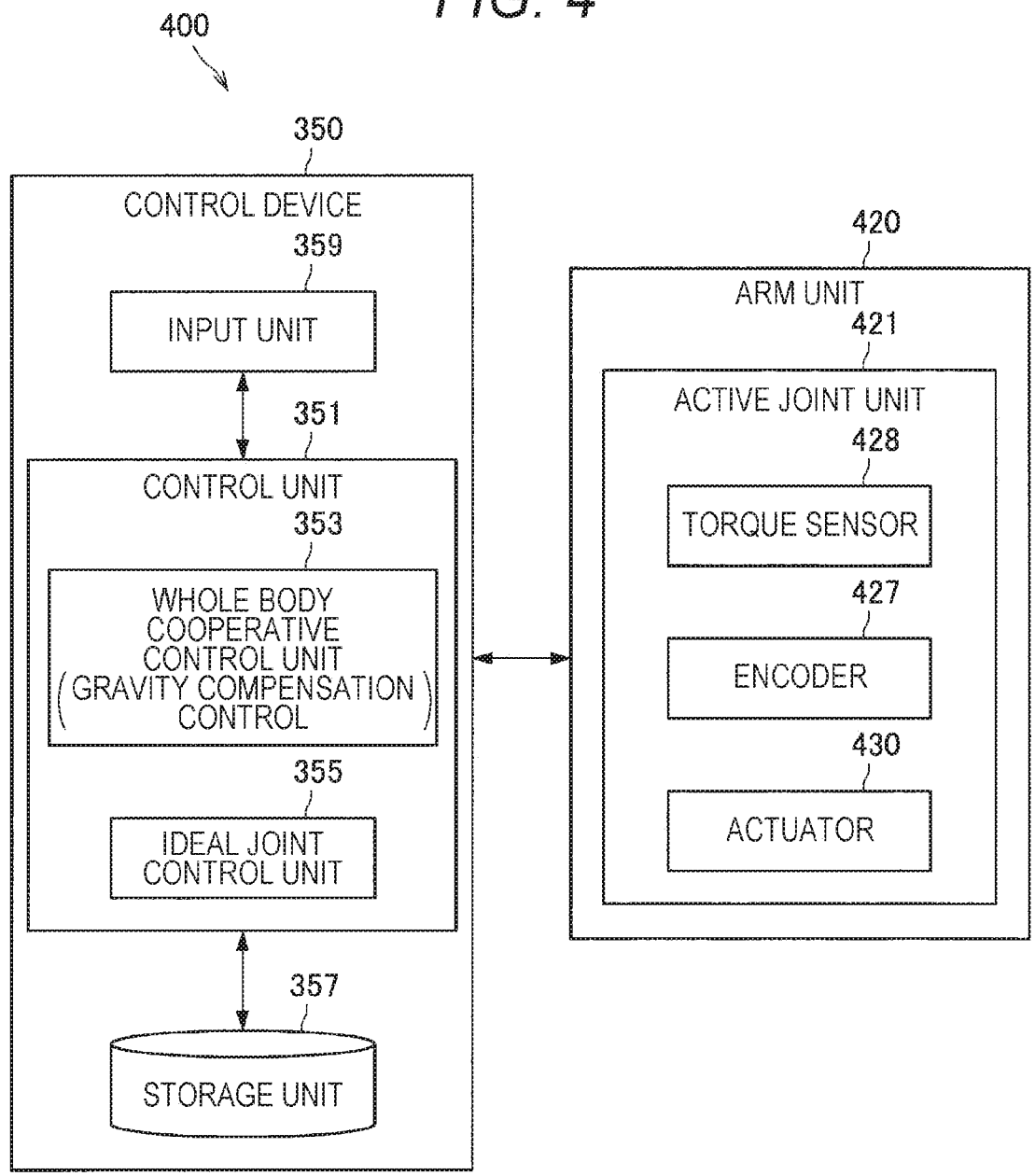
FIG. 4 is a block diagram illustrating a configuration example of the medical support arm device.

FIG. 4 is a block diagram illustrating an example of the overall configuration of the support arm device 400 including a control device 350. The control device 350 includes a control unit 351, a storage unit 357, and an input unit 359.

The control unit 351 is constituted by various signal processing circuits, for example, a CPU, a DSP, and the like. The control unit 351 integrally controls the control device 350 and performs various operations for controlling the drive of the arm unit 420 in the support arm device 400. Specifically, the control unit 351 includes a whole body cooperative control unit 353 and an ideal joint control unit 355. The whole body cooperative control unit 353 performs various operations in the whole body cooperative control in order for the drive control of the actuator 430 provided in the active joints 421a to 421f of the arm unit 420 of the support arm device 400. The ideal joint control unit 355 performs various operations in the ideal joint control that realizes an ideal response with respect to the whole body cooperative control by correcting influence of a disturbance. The storage unit 357 may be, for example, a storage element such as a random access memory (RAM) and a read only memory (ROM) or may be a semiconductor memory, a hard disk, or an external storage device.

The input unit 359 is an input interface that allows a user to input information, a command, and the like regarding the drive control of the support arm device 400 to the control unit 351. The input unit 359 may have operation means to be operated by the user, for example, a lever, a pedal, or the like, and a position, a speed, and the like of each constituent member of the arm unit 420 may be set as an instantaneous motion purpose depending on the operation of the lever, the pedal, and the like. The input unit 359 may have, for example, operation means to be operated by the user such as a mouse, a keyboard, a touch panel, a button, and a switch in addition to the lever and the pedal.

Furthermore, the arm unit 420 controlled by the control device 350 includes the active joints 421. The active joints 421 (421a to 421f) have various configurations necessary for the drive of the arm unit 420 such as support members for connecting or supporting the links 422a to 422f and the endoscope device 423. In the above description and the following description, the drive of the joint of the arm unit 420 may mean the drive of the actuator 430 in the active joints 421a to 421f.

The active joint 421 includes a torque sensor 428, an encoder 427, and the actuator 430. Note that the actuator 430, the encoder 427, and the torque sensor 428 are separately illustrated in FIG. 4, but the encoder 427 and the torque sensor 428 may be configured to be included in the actuator 430.

The actuator 430 is constituted by a motor, a motor driver, and a reduction gear. The actuator 430 is, for example, an actuator compatible with force control. In the actuator 430, the rotation of the motor is reduced by the reduction gear at a predetermined reduction ratio and is transmitted to another member in the subsequent stage via an output shaft, whereby the other member is driven.

The motor is a drive mechanism that produces a rotational drive force. The motor is driven to generate a torque corresponding to a torque command value from the control unit under the control of the motor driver. For example, a brushless motor is used as the motor. However, the present embodiment is not limited to such an example, and various known types of motors may be used as the motor.

The motor driver is a driver circuit (driver integrated circuit (IC)) that rotationally drives the motor by supplying a current to the motor, and a rotational speed of the motor can be controlled by adjusting the amount of the current to be supplied to the motor. The motor driver supplies a current corresponding to a torque command value τ from the control unit to the motor, thereby driving the motor.

Furthermore, the motor driver can adjust a viscous drag coefficient in a rotational motion of the actuator 430 by adjusting the amount of the current to be supplied to the motor. With the adjustment, it is possible to apply a predetermined resistance to the rotational motion of the actuator 430, in other words, rotational motions of the active joints 421a to 421f. For example, the active joints 421a to 421f can be set in the state of being easily rotated with an externally applied force (in other words, a state where the arm unit 420 is easily moved), and conversely, can be also set to the state of being hardly rotated against an externally applied force (in other words, a state where it is difficult to manually move the arm unit 420).

The reduction gear is connected to a rotation shaft (drive shaft) of the motor. The reduction gear decelerates a rotation speed of the rotation shaft of the connected motor (in other words, a rotation speed of an input shaft) at a predetermined reduction ratio and transmits the resultant to the output shaft. In the present embodiment, a configuration of the reduction gear is not limited to a specific one, and various types of known reduction gears may be used as the reduction gear. Meanwhile, it is preferable to use a device in which a reduction ratio can be set with high accuracy, for example, a harmonic drive (registered trademark) or the like, as the reduction gear. Furthermore, the reduction ratio of the reduction gear can be appropriately set in accordance with an application of the actuator 430. For example, if the actuator 430 is applied to the active joints 421a to 421f of the support arm device 400 as in the present embodiment, a reduction gear having a reduction ratio of about 1:100 can be preferably used.

The encoder 427 detects a rotation angle of the input shaft (in other words, a rotation angle of the rotation shaft of the motor). It is possible to obtain information, such as the rotation angle, rotation angular velocity, and rotation angular acceleration of the active joints 421a to 421f, on the basis of a rotational speed of the input shaft detected by the encoder 427 and the reduction ratio of the reduction gear. Various known rotary encoders, for example, a magnetic encoder, an optical encoder, and the like may be used as the encoder 427. Note that the encoder 427 may be provided only on the input shaft of the actuator 430, or an encoder to detect the rotation angle or the like of the output shaft of the actuator 430 may be further provided at the subsequent stage of the reduction gear.

The torque sensor 428 is connected to the output shaft of the actuator 430 and detects a torque acting on the actuator 430. The torque sensor 428 detects the torque (generation torque) output by the actuator 430. Furthermore, the torque sensor 428 can also detect an external torque applied to the actuator 430 from the outside.

The configuration of the active joint 421 has been described as above. Here, the operation of the arm unit 420 is controlled by force control in the present embodiment. Under the force control, rotation angles of the active joints 421a to 421f and torques acting on the active joints 421a to 421f are detected by the encoder 427 and the torque sensor 428 provided for each of the actuators 430 in the support arm device 400. At this time, the torque acting on each of the active joints 421a to 421f detected by the torque sensor 428 can also include a force acting on the arm unit 420 and/or the endoscope device 423.

Furthermore, a current state (a position, velocity, or the like) of the arm unit 420 can be obtained on the basis of the rotation angle detected by the encoder 427 and the torque value detected by the torque sensor 428. In the support arm device 400, a torque that needs to be generated by the actuator 430, provided in each of the active joints 421a to 421f, and is necessary for the arm unit 420 to perform a desired motion purpose is calculated on the basis of the acquired state of the arm unit 420 (arm state), and the actuator 430 of each of the active joints 421a to 421f is driven with the torque as a control value.

Note that various known actuators, generally used in various devices whose operations are controlled by force control, can be used the actuator 430. For example, those described in Japanese Patent Application Laid-Open Nos. 2009-269102 and 2011-209099, which are prior patent applications filed by the present applicant, and the like can be preferably used as the actuator 430.

In the support arm device 400 according to the present embodiment, the configuration of the actuator 430 and the configuration of each part constituting the actuator are not limited to the above configurations, and may be other configurations.

The basic configuration of the endoscopic surgery system has been described as above. Hereinafter, specific embodiments of the above-described endoscopic surgery system will be described.

2. First Embodiment

The present embodiment relates to setting of a virtual wall.

<2.1. Overview>

According to the present embodiment, provided is a medical arm system including a control unit that calculates a relative positional relationship between a distal end of a surgical instrument, connected to a multi-joint arm and inserted into a body of a patient, and the patient, and sets a movable range of the surgical instrument inside the patient's body in a distal end coordinate system of the surgical instrument on the basis of the calculation result of the relative positional relationship. The medical arm system sets a region, distant from an organ in a body cavity of the patient by a predetermined distance, as a movable range of the surgical instrument. With the configuration, it is also possible to prevent the surgical instrument from being separated too much from the organ while avoiding contact between the surgical instrument and the organ. The control unit of the medical arm system can be realized as the arm control device 5045 of the endoscopic surgery system 5000 or a processor such as a CPU equipped in the arm control device 5045. Furthermore, the control unit may be realized as an information processing device separate from the medical arm system.

More simply, the endoscopic surgery system 5000 according to the present embodiment sets the movable region on the basis of a relative position between the patient and the arm, and performs control such that an object (for example, a surgical instrument such as an endoscope and a surgical tool) does not exceed the movable region. It is possible to reduce a risk of organ damage by performing the control to prevent the excess of the movable region. Moreover, since it is possible to freely move the surgical instrument in a range that does not exceed the movable region, the convenience of the operator is improved.

A boundary that defines the movable region may be set as a virtual wall (virtual flat surface/virtual curved surface). Methods of setting the virtual wall are diversely conceivable.

For example, as a first setting method, the endoscopic surgery system 5000 defines a virtual wall for a region which is desirably not accessed by a surgical tool nor an endoscope on the basis of shape data in a body cavity of a patient, and performs an operation restriction. With the method, it is possible to easily set the virtual wall in a complex shape. Note that the shape data in the body cavity of the patient can be acquired at an arbitrary timing of either before surgery or during surgery, for example. The shape data is, for example, a computed tomography (CT) image or a magnetic resonance imaging (MRI) image. Since these are often captured before surgery, it is possible to eliminate an additional burden of setting the virtual wall.

For example, as a second setting method, the endoscopic surgery system 5000 defines a virtual wall for a region which is desirably not accessed by a surgical tool nor an endoscope on the basis of a measurement result such as an abdominal circumference of a patient, and performs an operation restriction. Since the measurement of the abdominal circumference can be easily executed in a short time, it becomes possible to set the virtual wall in a case of emergency surgery or even in a case where a CT image and an MRI image have not been captured.

For example, as a third setting method, the endoscopic surgery system 5000 defines a virtual wall in accordance with a distance from a distal end of an endoscope (surgical tool), and performs an operation restriction. With the method, the endoscopic surgery system 5000 can set a new virtual wall on the spot, for example, even in a case where a condition inside patient's body has changed during surgery.

Furthermore, the endoscopic surgery system 5000 can change the setting of the movable region.

Furthermore, the endoscopic surgery system 5000 can cancel the setting of the movable region.

<2.2. Details>

Hereinafter, technical characteristics of the endoscopic surgery system 5000 according to the present embodiment will be described in detail.

First, the endoscopic surgery system 5000 performs alignment between a patient with a CT image or an MRI image using a technology of navigation surgery. There are mainly two types of alignment methods of surface matching registration and paired point registration.

In the surface matching registration, processing is performed to measure a surface shape by tracing a skin surface of the patient with a surgical instrument and align the measurement result with a surface shape calculated from the CT image or the MRI image. Processing may be performed to acquire a skin surface shape with a three-dimensional sensor even without tracing the skin surface, and align the acquisition result with the surface shape calculated from the CT image or the MRI image.

In the paired point registration, a marker is pasted to a patient during CT or MRI capturing, and a plurality of matching pairs of points on the patient and points on an image is prepared, and registration is performed by aligning coordinates of the respective points.

The endoscopic surgery system 5000 performs alignment between the patient and a surgical instrument after completing the alignment between the patient and the CT image or the MRI image. Then, the endoscopic surgery system 5000 sets a virtual wall. Then, the endoscopic surgery system 5000 can operate a surgical tool or an endoscope such that a distal end of the endoscope (surgical tool) is included within a movable region defined by the virtual wall.

Specifically, the endoscopic surgery system 5000 may attach a marker on both the patient and the surgical instrument and determine a position and a posture of the surgical instrument relative to a position of the patient in relative coordinates. Furthermore, the endoscopic surgery system 5000 may set a position of the patient (specifically, patient surface) as a (specifically, patient surface) coordinate system, set a position of the surgical instrument as a surgical instrument coordinate system, and define a patient visceral space in a patient visceral part. Furthermore, the endoscopic surgery system 5000 may use a CT image or an MRI image to define a region where the surgical instrument is allowed to move and a region where the surgical instrument is not allowed to move in the patient visceral space, and describe an instrument movable region and an instrument non-movable region using the patient coordinate system.

Example of Method of Setting Virtual Wall

The methods of setting a virtual wall are diversely conceivable. The first to third setting methods will be described hereinafter.

(1) First Setting Method

In the first setting method, a virtual wall is set by utilizing a CT image (or an MRI image). Flow of the processing in the first setting method will be briefly described hereinafter.

First, the endoscopic surgery system 5000 measures a CT image. Next, the endoscopic surgery system 5000 creates a 3D organ from the CT image. Next, the endoscopic surgery system 5000 aligns a patient during surgery with the CT image. Next, the endoscopic surgery system 5000 defines the virtual wall on the basis of a coordinate system of the patient. Next, the endoscopic surgery system 5000 aligns the patient with an arm. Next, the endoscopic surgery system 5000 obtains a transform matrix from a coordinate system of the arm to the patient coordinate system. Next, the endoscopic surgery system 5000 describes a space of the virtual wall in the arm coordinate system using the transform matrix and uses the described space to control the arm. Then, the endoscopic surgery system 5000 describes a distal end of a surgical tool or an endoscope in the arm coordinate system and performs control so as not to exceed the virtual wall.

The processing in the first setting method will be described in detail hereinafter.

Alignment

Figure 5:
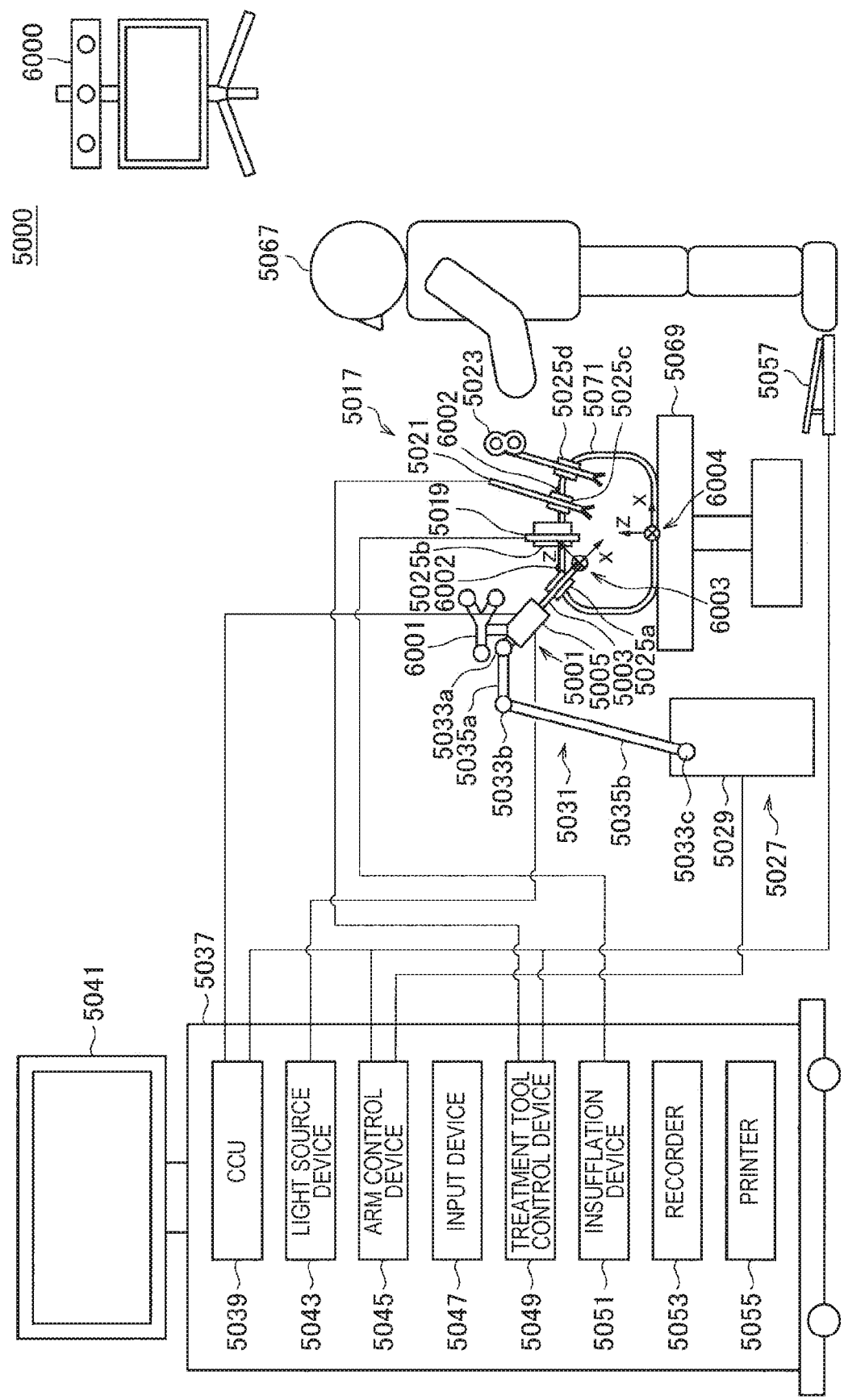
FIG. 5 is a diagram for describing an alignment method in a first setting method according to a first embodiment.

FIG. 5 is a diagram for describing an alignment method in the first setting method according to the present embodiment. As illustrated in FIG. 5, a marker 6001 for measurement of an arm position is attached to an arm distal end (for example, the camera head 5005). A position measurement device 6000 measures a position (and a posture) of the arm distal end on the basis of the marker 6001. Furthermore, a marker 6002 for measurement of a position (and a posture) of the patient is attached to the patient as illustrated in FIG. 5. The position measurement device 6000 measures the patient position on the basis of the marker 6002.

Next, the endoscopic surgery system 5000 sets an endoscope (surgical tool) distal end coordinate system indicated by reference sign 6003 to the measured position and posture of the arm distal end. Furthermore, the endoscopic surgery system 5000 sets a patient coordinate system indicated by reference sign 6004 to the measured position and posture of patient.

Then, the endoscopic surgery system 5000 obtains a transform matrix from the patient coordinate system to the endoscope (surgical tool) distal end coordinate system.

Setting of Virtual Wall

Figure 6:
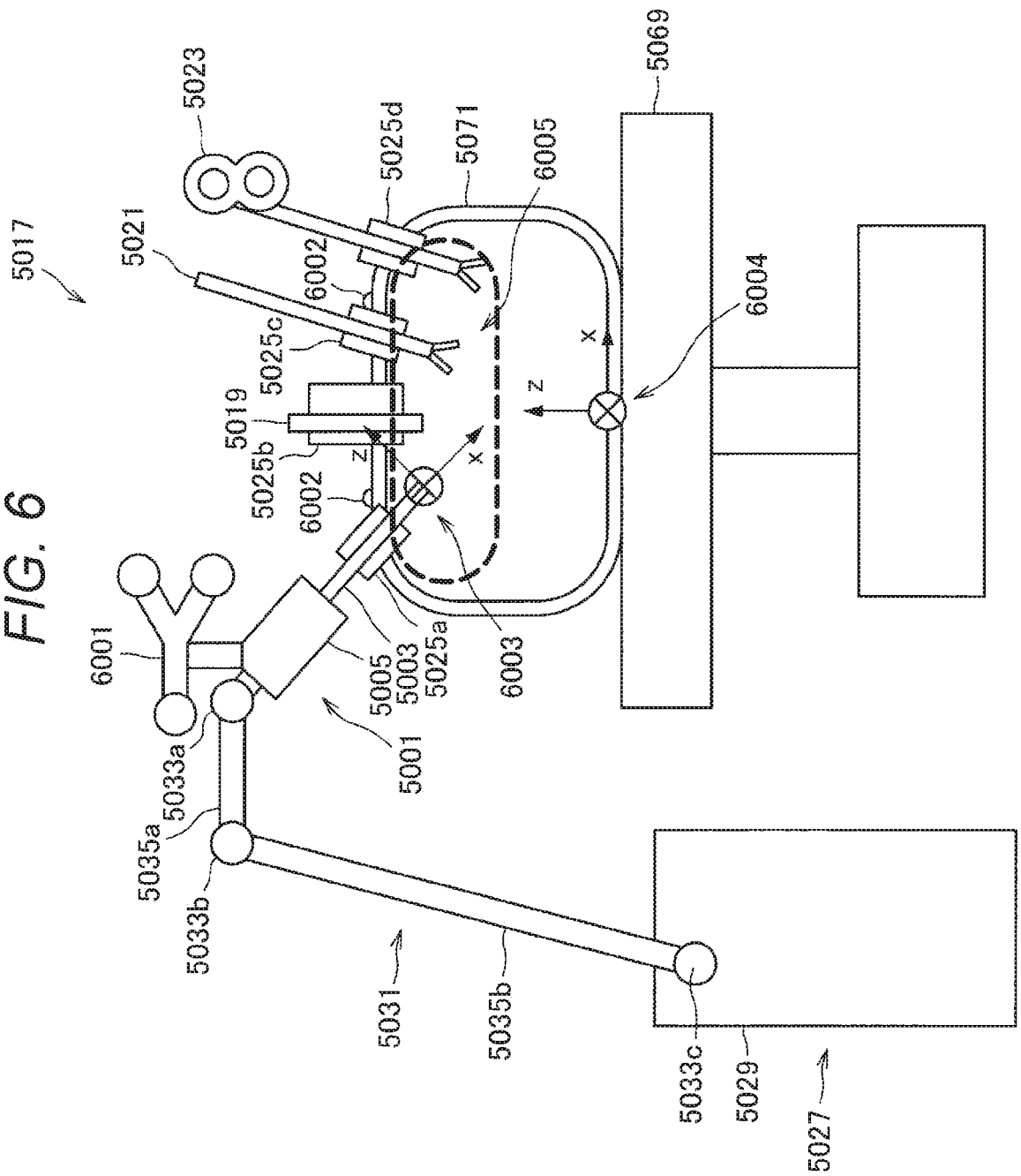
FIG. 6 is a diagram for describing setting of a virtual wall in the first setting method according to the first embodiment.

FIG. 6 is a diagram for describing the setting of the virtual wall in the first setting method according to the present embodiment. As illustrated in FIG. 6, the endoscopic surgery system 5000 sets a movable region indicated by reference sign 6005. Specifically, the endoscopic surgery system 5000 uses the patient coordinate system to describe the movable region, and sets the movable region (in other words, the virtual wall). At that time, the endoscopic surgery system 5000 can also perform 3D alignment with the CT image since the position of the patient has been accurately measured, and define the movable region using 3D data from CT. Furthermore, the endoscopic surgery system 5000 can also define the movable region simply according to a height from an operating table or the like.

The endoscopic surgery system 5000 performs coordinate conversion on the movable region described in the patient coordinate system indicated by reference sign 6004 using the transform matrix from the patient coordinate system to the endoscope (surgical tool) distal end coordinate system indicated by reference sign 6003 so as to handle the movable region in the endoscope (surgical tool) distal end coordinate system. Then, the endoscopic surgery system 5000 controls the arm distal end position so as not to exceed the movable region described in the endoscope (surgical tool) distal end coordinate system.

Flow of Processing

Figure 7:
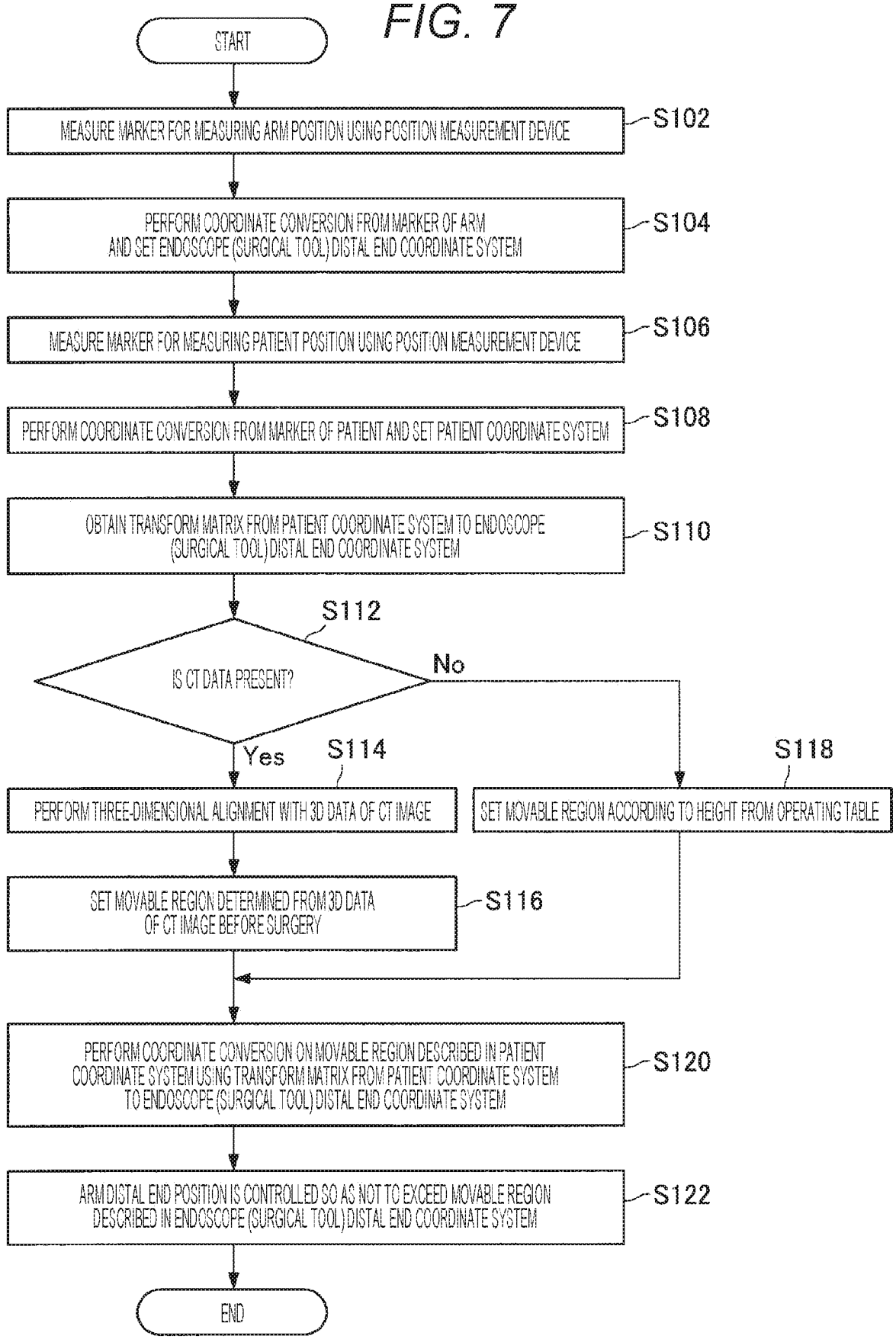
FIG. 7 is a flowchart illustrating an example of flow of a virtual wall setting process in the first setting method according to the first embodiment.

FIG. 7 is a flowchart illustrating an example of flow of the virtual wall setting process in the first setting method according to the present embodiment. As illustrated in FIG. 7, first, the endoscopic surgery system 5000 measures a marker for measurement of an arm position using the position measurement device 6000 (step S102). Next, the endoscopic surgery system 5000 performs coordinate conversion based on the marker of an arm and sets an endoscope (surgical tool) distal end coordinate system (step S104). Next, the endoscopic surgery system 5000 measures a marker for measurement of a patient position using the position measurement device 6000 (step S106). Next, the endoscopic surgery system 5000 performs coordinate conversion based on the marker of a patient, and sets a patient coordinate system (step S108). Next, the endoscopic surgery system 5000 obtains a transform matrix from the patient coordinate system to the endoscope (surgical tool) distal end coordinate system (step S110).

Next, the endoscopic surgery system 5000 determines whether or not there is CT data (step S112). In a case where it is determined that there is the CT data (step S112/YES), the endoscopic surgery system 5000 performs three-dimensional alignment with 3D data of a CT image (step S114). Next, the endoscopic surgery system 5000 sets a movable region determined from the 3D data of the CT image before surgery (step S116). On the other hand, in a case where it is determined that there is no CT data (step S112/NO), the endoscopic surgery system 5000 sets a movable region based on a height from an operating table (step S118).

After setting the movable region, the endoscopic surgery system 5000 performs coordinate conversion on the movable region described in the patient coordinate system using the transform matrix from the patient coordinate system to the endoscope (surgical tool) distal end coordinate system (step S120). Then, the endoscopic surgery system 5000 controls the arm distal end position so as not to exceed the movable region described in the endoscope (surgical tool) distal end coordinate system (step S122).

(2) Second Setting Method

In the second setting method, a simple virtual wall is set. Flow of the processing in the second setting method will be briefly described hereinafter.

First, an abdominal circumference of a patient is measured. Next, the endoscopic surgery system 5000 sets a height of the virtual wall and defines the height of the virtual wall relative to an operating table. Next, the endoscopic surgery system 5000 aligns an arm with the operating table. Next, the endoscopic surgery system 5000 describes the virtual wall in a coordinate system of the arm and uses the described virtual wall to control the arm. Then, the endoscopic surgery system 5000 describes a distal end of a surgical tool or an endoscope in the arm coordinate system and performs control so as not to exceed the virtual wall. Note that, as a method of measuring the abdominal circumference, it is possible to consider (1) a method in which a doctor or a medical staff measures an abdominal circumference of a patient and inputs the measured abdominal circumference to an endoscopic surgery system before surgery, (2) a method of separately providing a camera (including a stereo camera), a depth sensor, and the like to an endoscopic surgery system and measuring an abdominal circumference of a patient, (3) a method of touching (tracing) the abdomen of a patient with a distal end of an arm to measure an abdominal circumference, and the like. Furthermore, a height of the abdomen from the operating table in a state where a patient lies down is measured (1) by the camera (including the stereo camera) and the depth sensor, or (2) the height is measured by aligning the distal end of the arm with the abdomen, and the endoscopic surgery system 5000 can also define the height of the virtual wall on the basis of the measurement result.

The processing in the second setting method will be described in detail hereinafter.

Alignment

Figure 8:
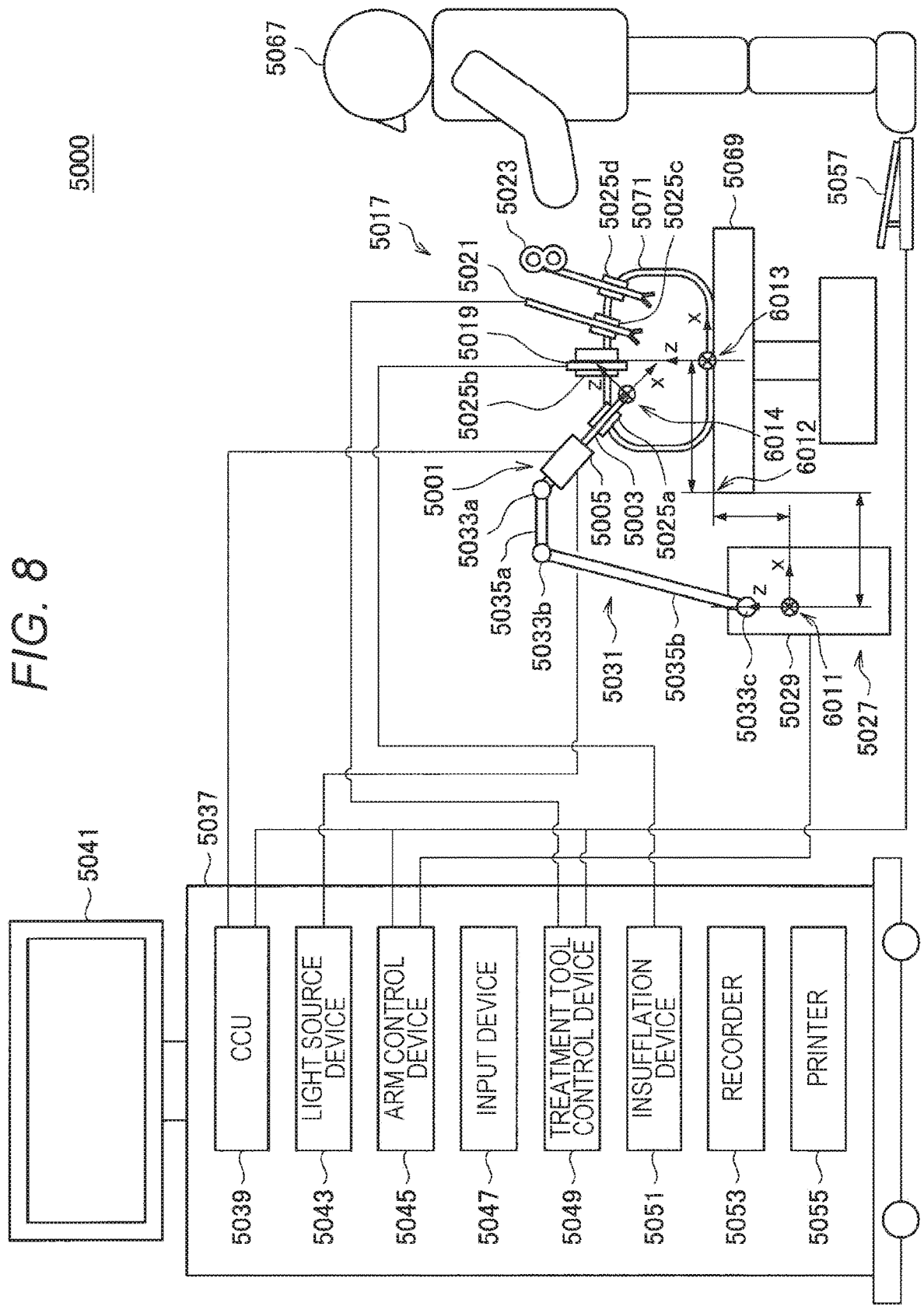
FIG. 8 is a diagram for describing an alignment method in a second setting method according to the first embodiment.

FIG. 8 is a diagram for describing an alignment method in the second setting method according to the present embodiment. As illustrated in FIG. 8, an arm reference position indicated by reference sign 6011, an operating table reference position indicated by reference sign 6012, and a patient reference position indicated by reference sign 6013 are defined in the present method. The endoscopic surgery system 5000 measures a positional relationship (x,y,z) between the arm reference position and the operating table reference position. Furthermore, the endoscopic surgery system 5000 measures a positional relationship (x,y,z) between the operating table reference position and the patient reference position. Note that x and y in the patient reference position indicates x and y positions of the navel of a patient, and z is a height of the operating table in the example illustrated in FIG. 8.

Next, the endoscopic surgery system 5000 obtains a transform matrix from an arm reference position coordinate system to an endoscope (surgical tool) distal end coordinate system indicated by reference sign 6014. Furthermore, the endoscopic surgery system 5000 determines a transform matrix from the arm reference position coordinate system to a patient reference position, and sets the patient coordinate system.

Then, the endoscopic surgery system 5000 obtains a transform matrix from the patient coordinate system to the endoscope (surgical tool) distal end coordinate system.

Setting of Virtual Wall

Figure 9:
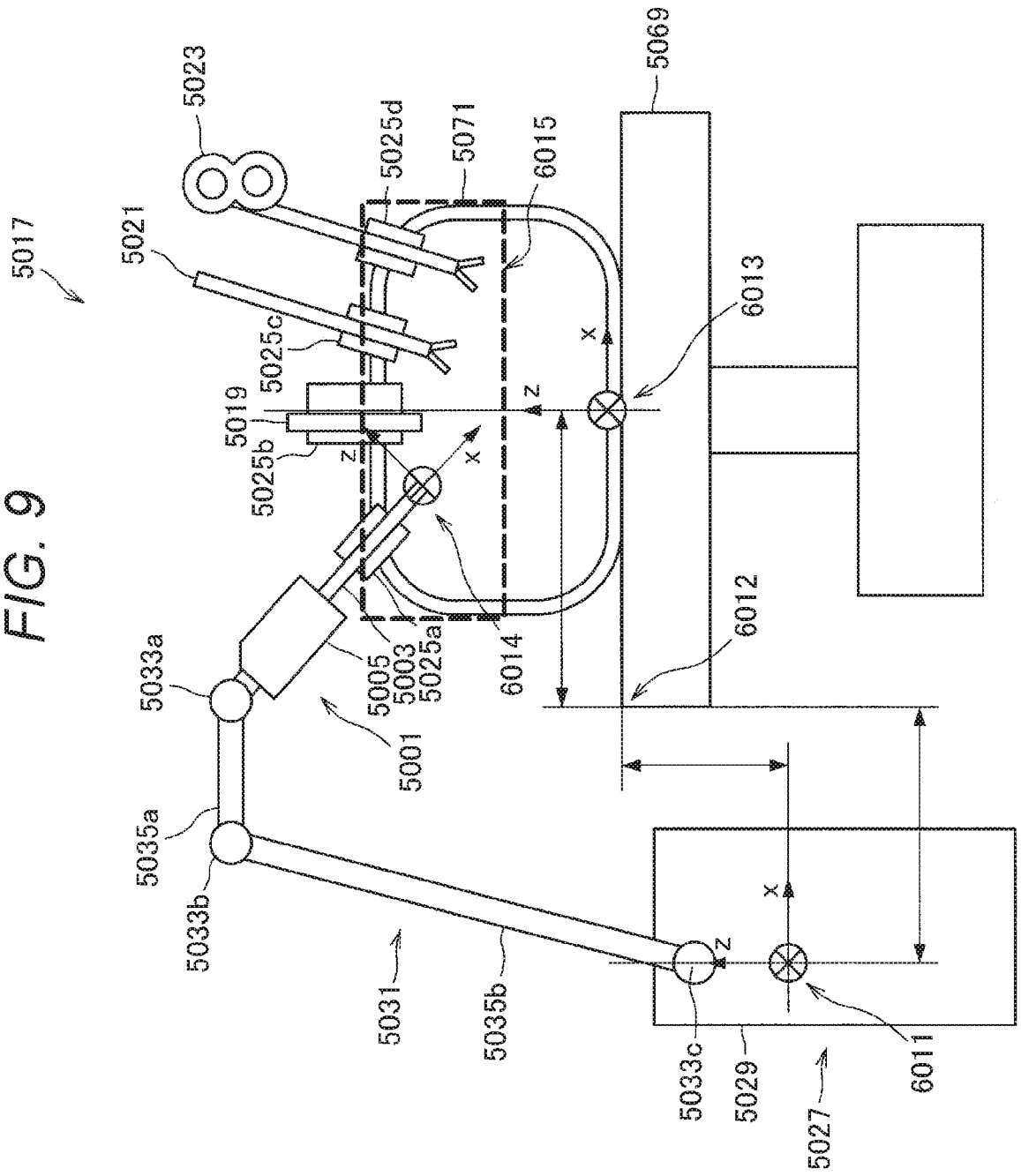
FIG. 9 is a diagram for describing setting of a virtual wall in the second setting method according to the first embodiment.

FIG. 9 is a diagram for describing the setting of the virtual wall in the second setting method according to the present embodiment. As illustrated in FIG. 9, the endoscopic surgery system 5000 sets a movable region indicated by reference sign 6015. Physically, the endoscopic surgery system 5000 uses the patient coordinate system to describe the movable region, and sets the movable region (in other words, the virtual wall). At that time, the endoscopic surgery system 5000 can also define the movable region simply according to a height from an operating table or the like. Furthermore, the endoscopic surgery system 5000 can also define the movable region based on a height according to a waist circumference using the waist circumference of a patient measured before surgery.

The endoscopic surgery system 5000 performs coordinate conversion on the movable region described in the patient coordinate system using the transform matrix from the patient coordinate system to the endoscope (surgical tool) distal end coordinate system so as to handle the movable region in the endoscope (surgical tool) distal end coordinate system. Then, the endoscopic surgery system 5000 controls the arm distal end position so as not to exceed the movable region described in the endoscope (surgical tool) distal end coordinate system.

Flow of Processing

Figure 10:
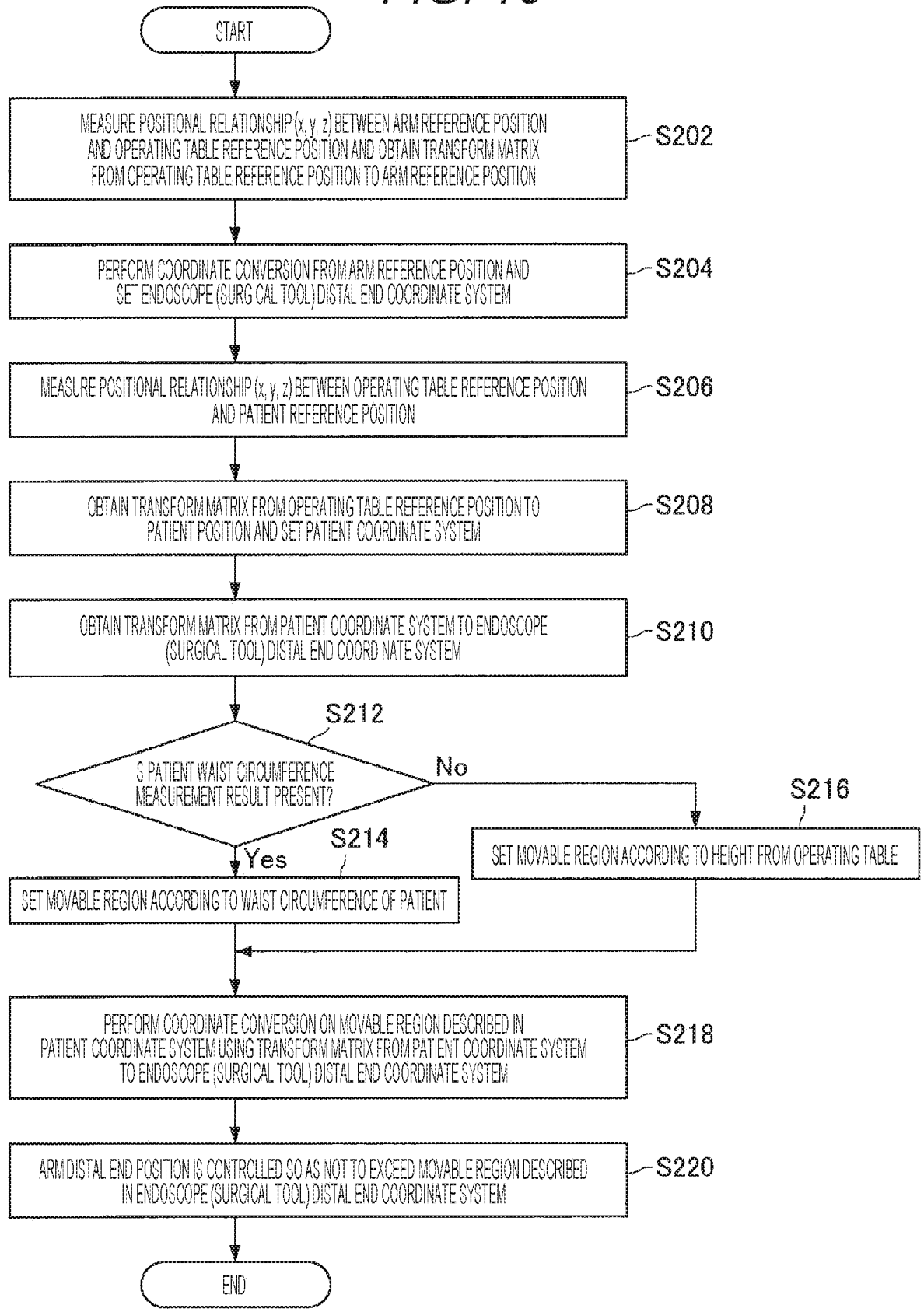
FIG. 10 is a flowchart illustrating an example of flow of a virtual wall setting process in the second setting method according to the first embodiment.

FIG. 10 is a flowchart illustrating an example of flow of the virtual wall setting process in the second setting method according to the present embodiment. As illustrated in FIG. 10, first, the endoscopic surgery system 5000 measures a positional relationship (x,y,z) between the arm reference position and the operating table reference position, and obtains a transform matrix from the operating table reference position to the arm reference position (step S202). Next, the endoscopic surgery system 5000 performs coordinate conversion from the arm reference position, and sets an endoscope (surgical tool) distal end coordinate system (step S204). Next, the endoscopic surgery system 5000 measures a positional relationship (x,y,z) between the operating table reference position and the patient reference position (step S206). Next, the endoscopic surgery system 5000 obtains a transform matrix from the operating table reference position to the patient position, and sets a patient coordinate system (step S208). Next, the endoscopic surgery system 5000 obtains a transform matrix from the patient coordinate system to the endoscope (surgical tool) distal end coordinate system (step S210).

Next, the endoscopic surgery system 5000 determines whether or not there is a measurement result of a patient waist circumference (step S212). In a case where it is determined that there is the measurement result of the patient waist circumference (step S212/YES), the endoscopic surgery system 5000 sets a movable region according to the patient waist circumference (step S214). On the other hand, in a case where it is determined that there is no measurement result of the patient waist circumference (step S212/NO), the endoscopic surgery system 5000 sets a movable region according to a height from the operating table (step S216).

After setting the movable region, the endoscopic surgery system 5000 performs coordinate conversion on the movable region described in the patient coordinate system using the transform matrix from the patient coordinate system to the endoscope (surgical tool) distal end coordinate system (step S218). Then, the endoscopic surgery system 5000 controls the arm distal end position so as not to exceed the movable region described in the endoscope (surgical tool) distal end coordinate system (step S220).

(3) Third Setting Method

In the third setting method, a virtual wall according to a distance is set. Flow of the processing in the third setting method will be briefly described hereinafter.

First, the endoscopic surgery system 5000 sets an endoscope distal end coordinate system. Next, the endoscopic surgery system 5000 measures a distance to an organ using a distance sensor. Next, the endoscopic surgery system 5000 defines the virtual wall according to the distance. Next, the endoscopic surgery system 5000 describes a space of the virtual wall in the arm coordinate system using the transform matrix and uses the described space to control the arm. Then, the endoscopic surgery system 5000 describes a distal end of a surgical tool or an endoscope in the arm coordinate system and performs control so as not to exceed the virtual wall.

The processing in the third setting method will be described in detail hereinafter.

Setting of Virtual Wall

Figure 11:
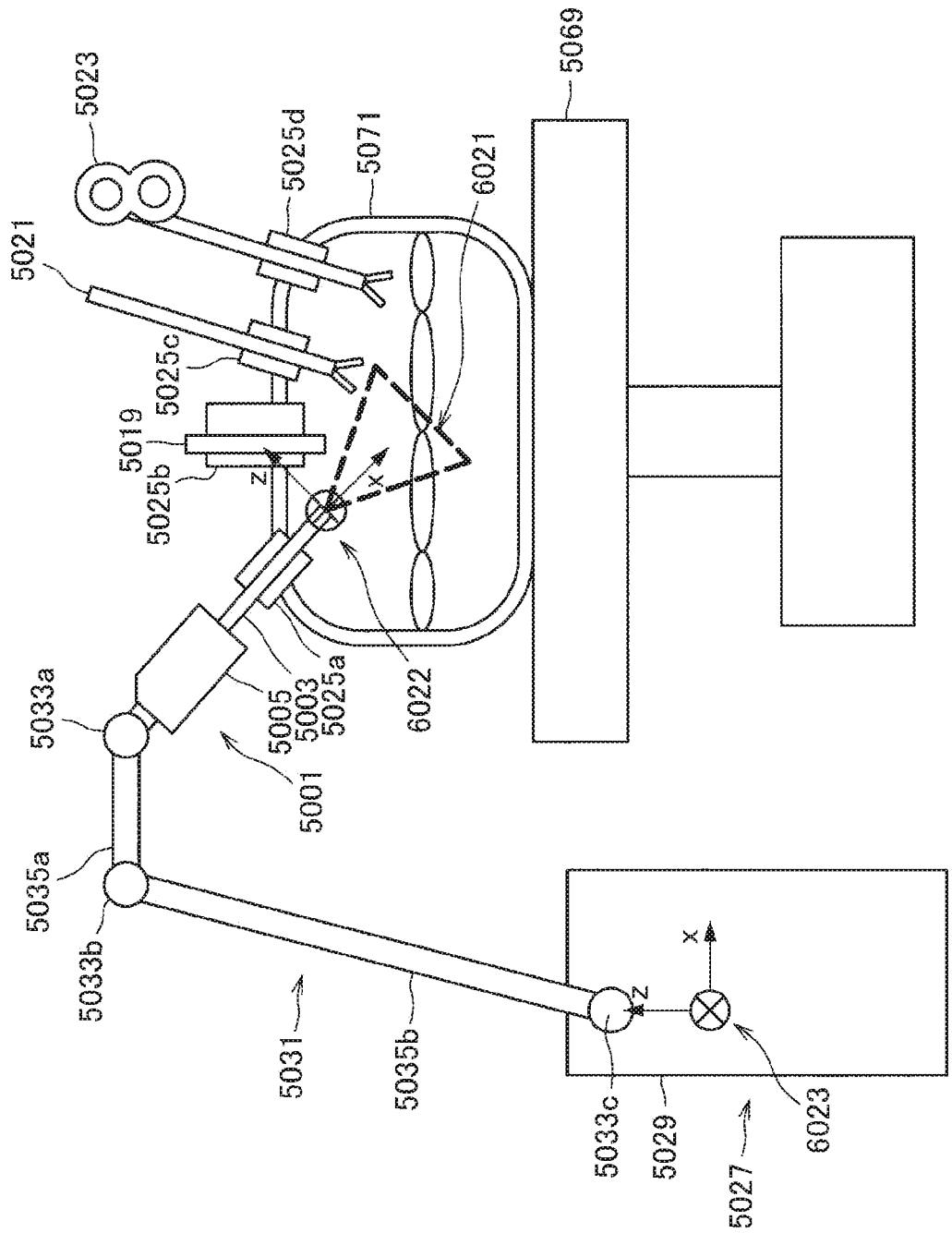
FIG. 11 is a diagram for describing setting of a virtual wall in a third setting method according to the first embodiment.

FIG. 11 is a diagram for describing the setting of the virtual wall in the third setting method according to the present embodiment. As illustrated in FIG. 11, the endoscopic surgery system 5000 sets a movable region indicated by reference sign 6021. Specifically, the endoscopic surgery system 5000 first measures a distance from a distal end of an endoscope to the organ in a patient's body using the distance sensor. With the measurement, the endoscopic surgery system 5000 grasps a size of an open space in the patient's body. Note that a technology such as a depth sensor, a 3D endoscope (stereo), autofocus distance, monocular stereo, and simultaneous localization and mapping (SLAM) can be utilized for the distance measurement. Then, the endoscopic surgery system 5000 describes the movable region according to the distance in an endoscope distal end coordinate system indicated by reference sign 6022.

Then, the endoscopic surgery system 5000 controls the arm distal end position so as not to exceed the movable region described in the endoscope distal end coordinate system.

The setting of the virtual wall in the third setting method will be described in more detail with reference to FIG. 12.

Figure 12:
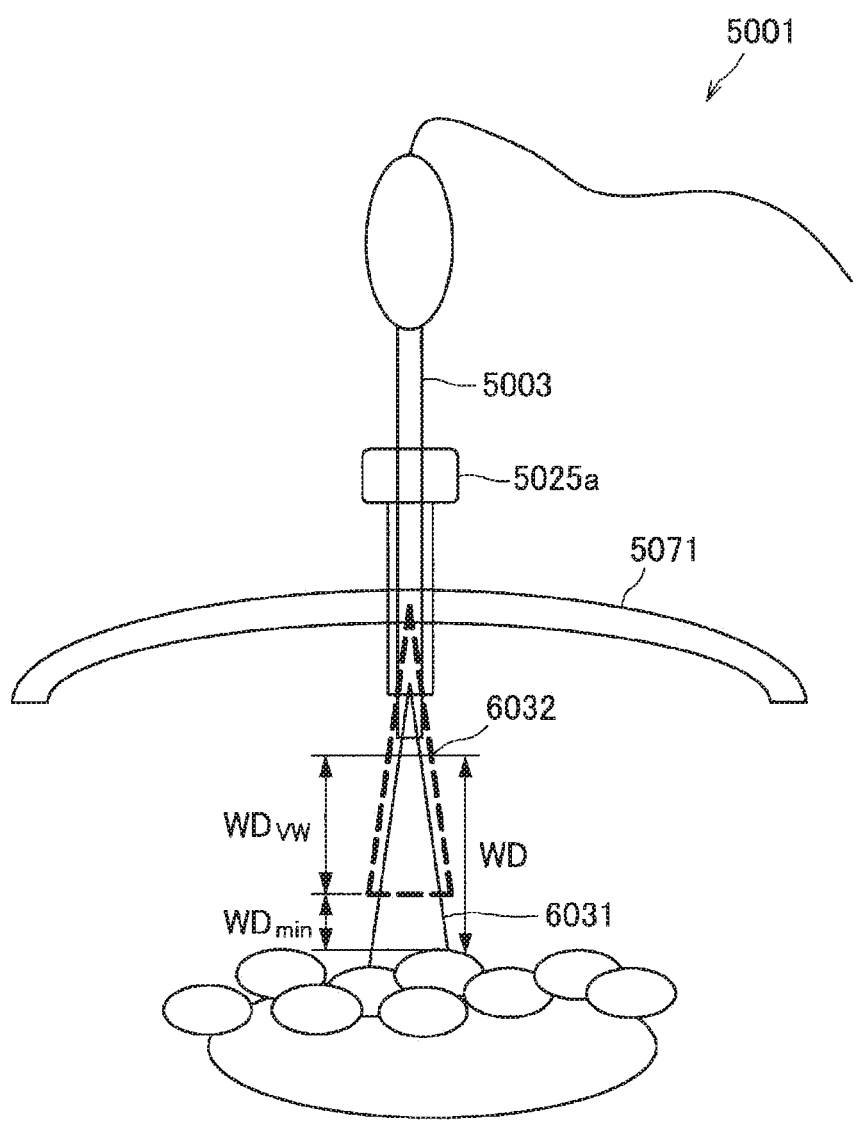
FIG. 12 is a diagram for describing setting of a virtual wall in the third setting method according to the first embodiment.

FIG. 12 is a diagram for describing the setting of the virtual wall in the third setting method according to the present embodiment. FIG. 12 illustrates a state where the lens barrel 5003 of the endoscope 5001 is inserted into a body cavity of the patient 5071 through the trocar 5025a tapped in the abdominal wall of the patient 5071. The endoscopic surgery system 5000 measures a distance WD (working distance) from an endoscope distal end to an organ. Next, the endoscopic surgery system 5000 sets a distance obtained by subtracting $WD_{min}$, which is the minimum distance of the endoscope (the minimum distance for focusing), from the measured distance WD as a virtual wall setting distance $WD_{VW}$. Then, the endoscopic surgery system 5000 sets a virtual wall 6032 on the basis of the virtual wall setting distance $WD_{VW}$ and an angle of view 6031 of the endoscope. A region included in the virtual wall 6032 is the movable region of the endoscope. With such setting, it is possible to prevent the endoscope 5001 from approaching the organ up to a distance at which focusing is not achieved.

Note that the endoscope 5001 includes a distance measurement sensor, and the distance WD is measured by the distance measurement sensor. The distance measurement sensor may be provided in the camera head 5005 or may be provided in the lens barrel 5003. Furthermore, an imaging device (for example, the above-described imaging unit 5009) provided in the endoscope 5001 may function as the distance measurement sensor. Various technologies such as a time of flight (TOF) method, distance measurement based on an auto-focus distance, distance measurement based on a stereo image, and use of a simultaneous localization and mapping (SLAM) technology may be adopted as a distance measurement method. Since the endoscope 5001 is equipped with the distance measurement sensor, the endoscopic surgery system 5000 can grasp the size of the open space in the patient's body and can use the size as information to set the virtual wall.

Flow of Processing

Figure 13:
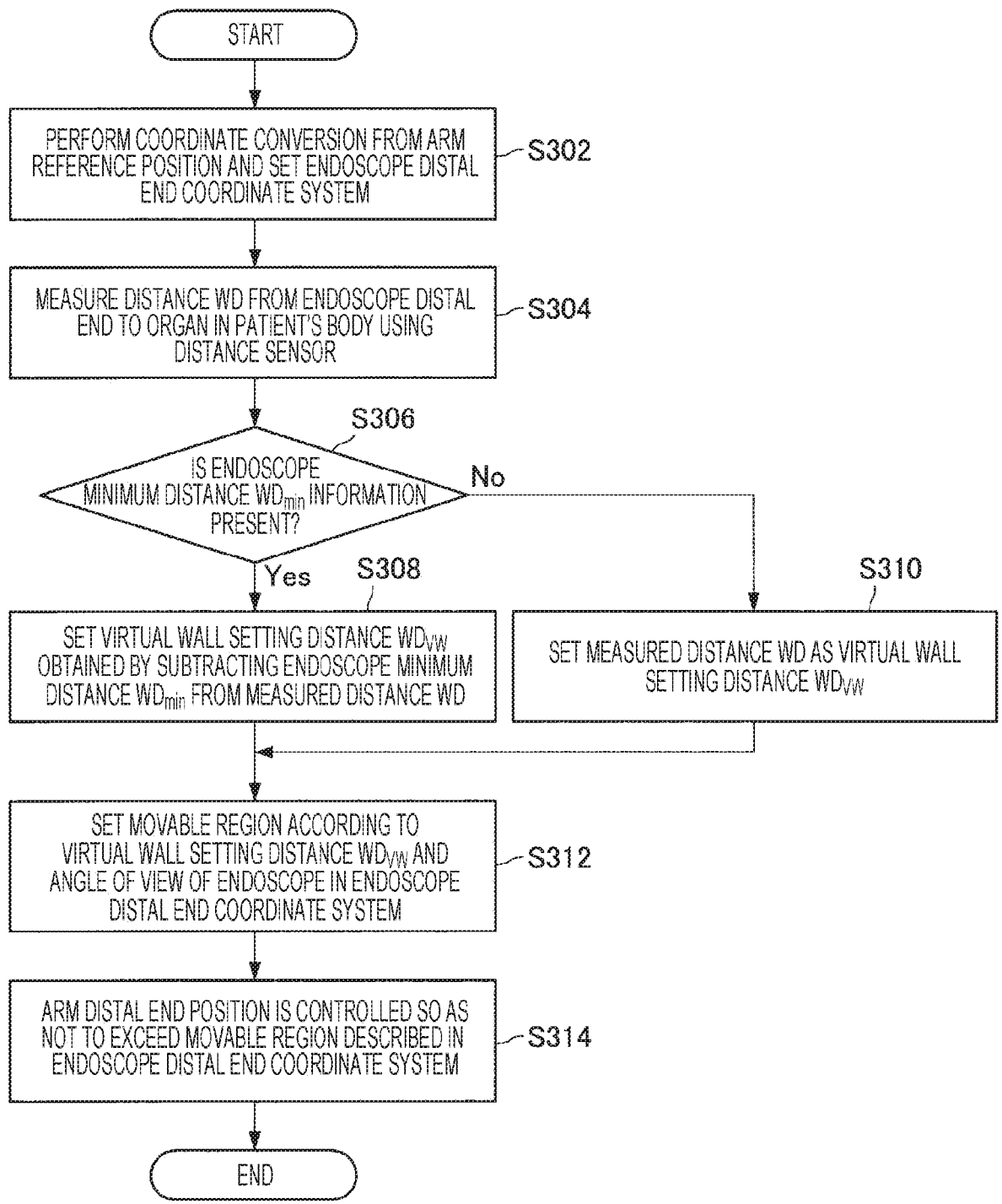
FIG. 13 is a flowchart illustrating an example of flow of a virtual wall setting process in the third setting method according to the first embodiment.

FIG. 13 is a flowchart illustrating an example of flow of the virtual wall setting process in the third setting method according to the present embodiment. As illustrated in FIG. 13, the endoscopic surgery system 5000 first performs coordinate conversion from the arm reference position, and sets an endoscope distal end coordinate system (step S302). Next, the endoscopic surgery system 5000 measures the distance WD from the distal end of the endoscope to the organ in the patient's body using the distance sensor (step S304).

Next, the endoscopic surgery system 5000 determines whether or not there is endoscope minimum distance $WD_{min}$ information (step S306). In a case where it is determined that there is the endoscope minimum distance $WD_{min}$ information (step S306/YES), the endoscopic surgery system 5000 sets the virtual wall setting distance $WD_{vw}$ obtained by subtracting the endoscope minimum distance $WD_{min}$ from the measured distance WD (step S308). On the other hand, in a case where it is determined that the endoscope minimum distance $WD_{min}$ is not present (step S306/NO), the endoscopic surgery system 5000 sets the measured distance WD as the virtual wall setting distance $WD_{VW}$ (step S310).

Next, the endoscopic surgery system 5000 sets a movable region according to the virtual wall setting distance $WD_{VW}$ and an angle of view of the endoscope in the endoscope distal end coordinate system (step S312). Then, the endoscopic surgery system 5000 controls the arm distal end position so as not to exceed the movable region described in the endoscope distal end coordinate system (step S314).

Image Regarding Setting of Virtual Wall

Hereinafter, an image regarding setting of a virtual wall will be described with reference to FIGS. 14 to 20. FIGS. 14 to 20 are diagrams for describing the setting of the virtual wall according to the present embodiment.

Figure 14:
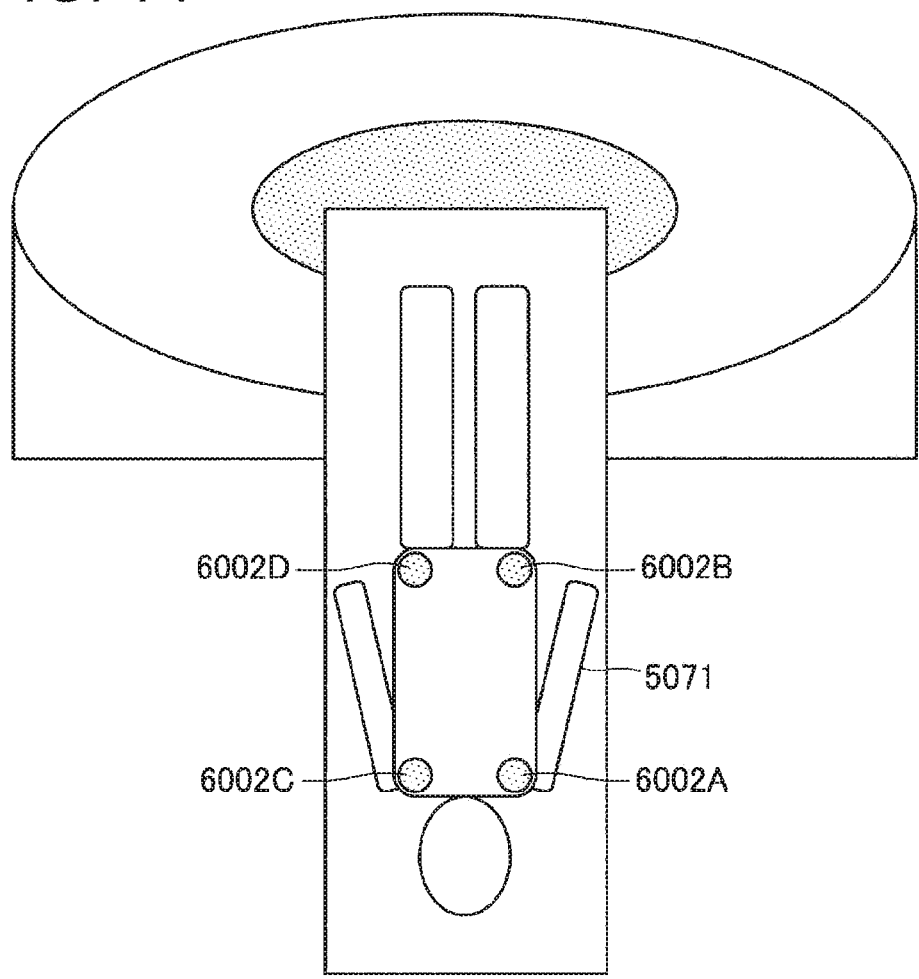
FIG. 14 is a diagram for describing setting of a virtual wall according to the first embodiment.
Figure 15:
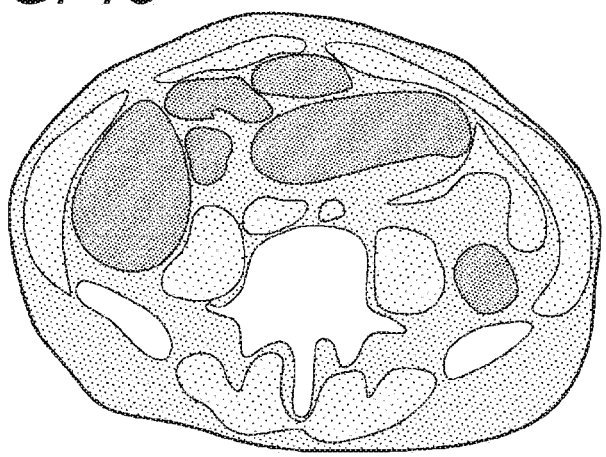
FIG. 15 is a diagram for describing setting of a virtual wall according to the first embodiment.
Figure 15:
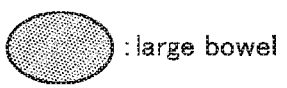
Figure 16:
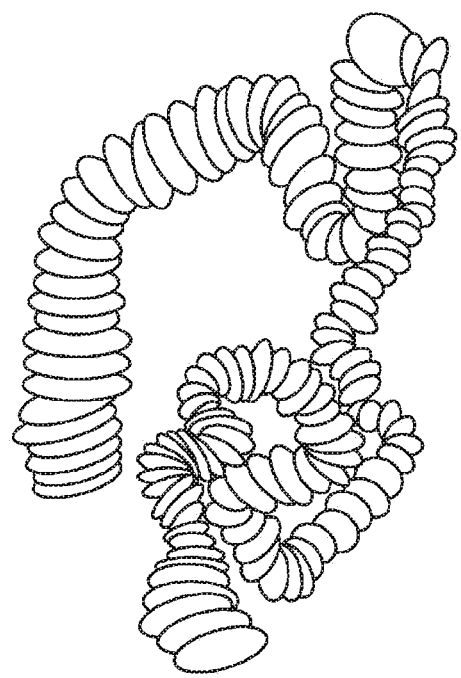
FIG. 16 is a diagram for describing setting of a virtual wall according to the first embodiment.
Figure 17:
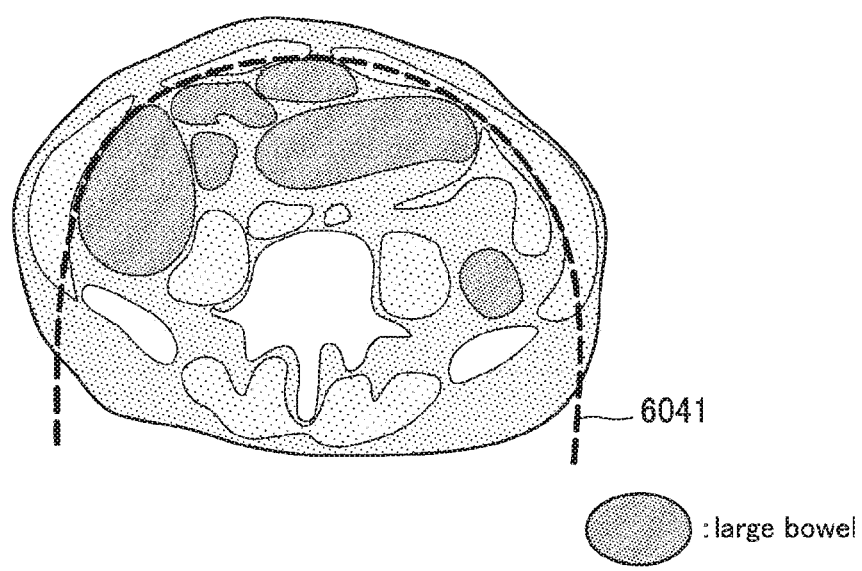
FIG. 17 is a diagram for describing setting of a virtual wall according to the first embodiment.
Figure 18:
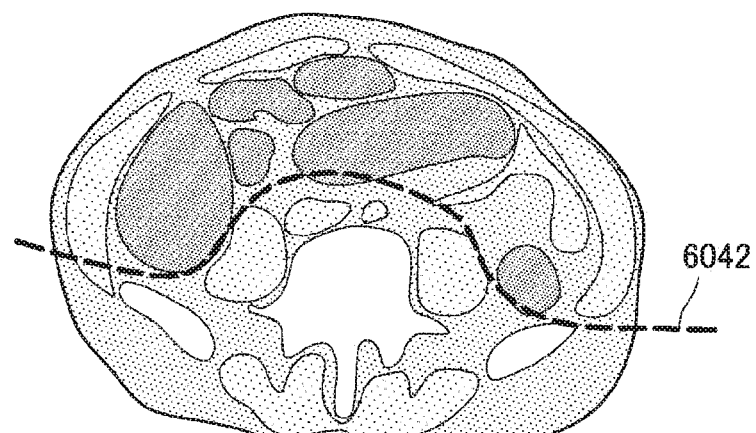
FIG. 18 is a diagram for describing setting of a virtual wall according to the first embodiment.
Figure 18:
Figure 19:
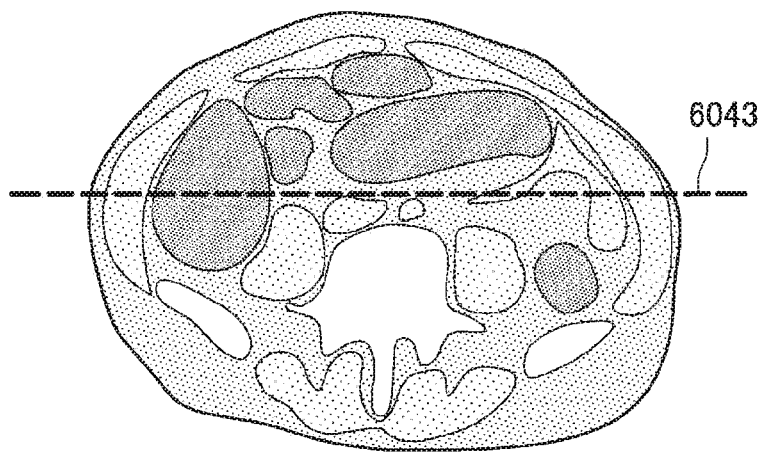
FIG. 19 is a diagram for describing setting of a virtual wall according to the first embodiment.
Figure 19:
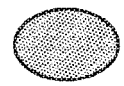
Figure 20:
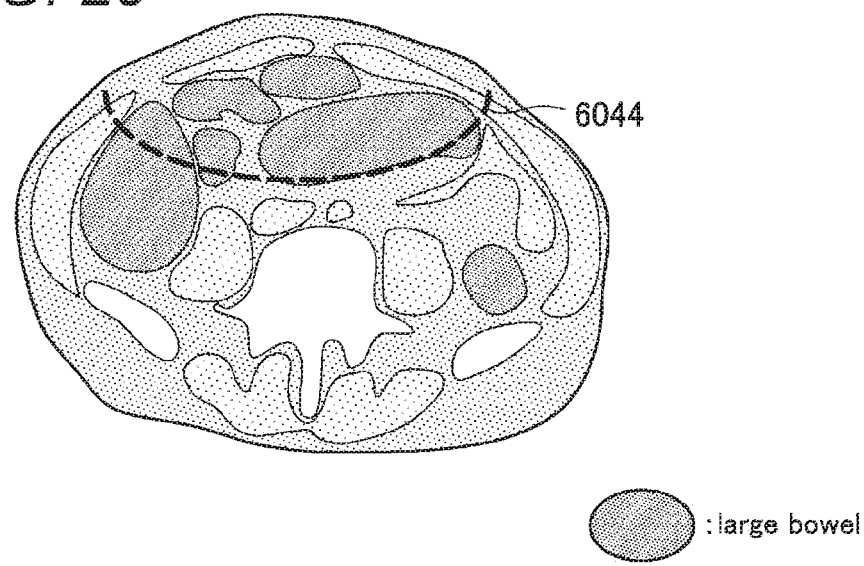
FIG. 20 is a diagram for describing setting of a virtual wall according to the first embodiment.

As illustrated in FIG. 14, for example, four markers 6002 (6002A to 6002D) are attached to the patient 5071 at the time of registration. FIG. 15 is an example of a CT image with the vicinity of the large intestine as an object to be imaged. FIG. 16 is an image of the large intestine three-dimensionally formed from the CT image. The endoscopic surgery system 5000 uses the marker attached to the patient's body to align a position of the large intestine measured before surgery with a position of the patient's body during surgery. FIG. 17 is a first example of the virtual wall to be set. In the first example, a virtual wall 6041 which does not touch even the large intestine is set. FIG. 18 is a second example of the virtual wall to be set. In the second example, a virtual wall 6042 which touches the large intestine but does not touch organs behind the large intestine is set. FIG. 19 is a third example of the virtual wall to be set. In the third example, a simple virtual wall 6043 is set. This simple virtual wall 6043 can be adjusted in height in accordance with a measured abdominal circumference. FIG. 20 illustrates a fourth example of the virtual wall to be set. In the fourth example, a simple virtual wall 6044 is set. This simple virtual wall 6044 is set to draw an arc from a central position of the body, and the arc can be adjusted in accordance with a measured abdominal circumference.

Supplement Regarding Setting of Virtual Wall

It is desirable that the endoscopic surgery system 5000 easily perform setting of a virtual wall in a direction in which operation ranges of an endoscope and a surgical tool are narrowed during surgery. For example, the endoscopic surgery system 5000 resets the virtual wall that defines a boundary of a movable region such that the movable region is narrowed during surgery. With the configuration, the operator can easily perform setting to safely conduct surgery.

Furthermore, it is desirable that the endoscopic surgery system 5000 carefully perform setting of a virtual wall in a direction in which the operation ranges of the endoscope and the surgical tool are widened during surgery. For example, it is desirable to make it impossible to perform the setting easily by requiring selection of OK or NG in a UI and performing the setting only in a case where OK is selected. When the virtual wall is set in the direction in which the operation range is widened, a risk that a surgical instrument contacts an organ is relatively high, but it is possible to prevent such a setting from being erroneously performed by confirming the operation.

Furthermore, it is desirable that the endoscopic surgery system 5000 be capable of canceling the virtual wall.

Control of Arm Distal End Position

The endoscopic surgery system 5000 controls the arm distal end position so as not to exceed the virtual wall (in other words, the movable region) described in the endoscope (surgical tool) distal end coordinate system. Specifically, the endoscopic surgery system 5000 sets a motion purpose inside an operation space as in the following Formula (1).

[Formula 1]

$$\begin{cases} \ddot{x} = K_v(\dot{x}_d - \dot{x}) + K_p(x_d - x_w) & \Delta x \geq 0 \\ \ddot{x} = K_v(\dot{x}_d - \dot{x}) & \Delta x < 0 \end{cases} \quad (1)$$

Here, the left side of Formula (1) is the motion purpose inside the operation space. Furthermore, $\Delta x = x_w - x$, which represents a difference between a virtual wall setting position $x_w$ and a current endoscope (surgical tool) distal end position x. Furthermore, it is possible to change a characteristic (for example, hardness) at the time of reaching the virtual wall using setting values of $K_p$ and $K_v$.

Since a torque $\tau_\alpha$ acting on each joint through all-axis cooperative control is calculated from the motion purpose illustrated in the above Formula (1), the entire arm takes a motion receiving a reaction force corresponding to the motion purpose illustrated in the above Formula (1).

Effect

According to the present embodiment, the endoscopic surgery system 5000 can reduce a risk of organ damage. Furthermore, the endoscopic surgery system 5000 can reduce stress of a doctor operating an endoscope and a surgical tool during surgery. Furthermore, the endoscopic surgery system 5000 enables an operator to operate the endoscope and the surgical tool at ease even for an operation without sense of touch such as a joystick, and a master-slave operation.

The technology according to the present embodiment is particularly advantageous for an endoscope since an object to be controlled is prevented from touching an organ. Furthermore, the technology according to the present embodiment can realize usage of protecting a part that is easily damaged, for example, the pancreas or the like, or protecting a part that is likely to occur nerve damage or the like against forceps or a surgical tool.

3. Second Embodiment

<3.1. Overview>

The present embodiment relates to use of a virtual wall.

According to the present disclosure, proposed is a medical arm system including a control unit which sets a virtual plane in a body cavity of a patient and controls a multi-joint arm so as to constrain a predetermined point in the body cavity on the virtual plane in an endoscope attached to the multi-joint arm and inserted into the body cavity of the patient. In a case where the appropriate virtual plane (for example, the virtual wall described in the first embodiment) is set, it is possible to mitigate a risk of organ damage by constraining the predetermined point of the endoscope in the body cavity on the virtual plane. Moreover, the medical arm system according to the present embodiment controls the multi-joint arm such that an object in the body cavity (in other words, an observation object) is present in a central area (at the center or near the center) of an image obtained by the endoscope. With the control, it becomes possible to take an object such as a surgical instrument and a tumor into the central region of the image obtained by the endoscope, and the convenience of the operator is improved. The control unit of the medical arm system can be realized as the arm control device 5045 of the endoscopic surgery system 5000 or a processor such as a CPU equipped in the arm control device 5045. Furthermore, the control unit may be realized as an information processing device separate from the medical arm system. The predetermined point to be constrained on the virtual plane is also referred to as a point to be constrained hereinafter.

An overview of the present embodiment will be described below with reference to FIGS. 21 and 22. Note that it is assumed that the point to be constrained is a distal end of the endoscope.

Figure 21:
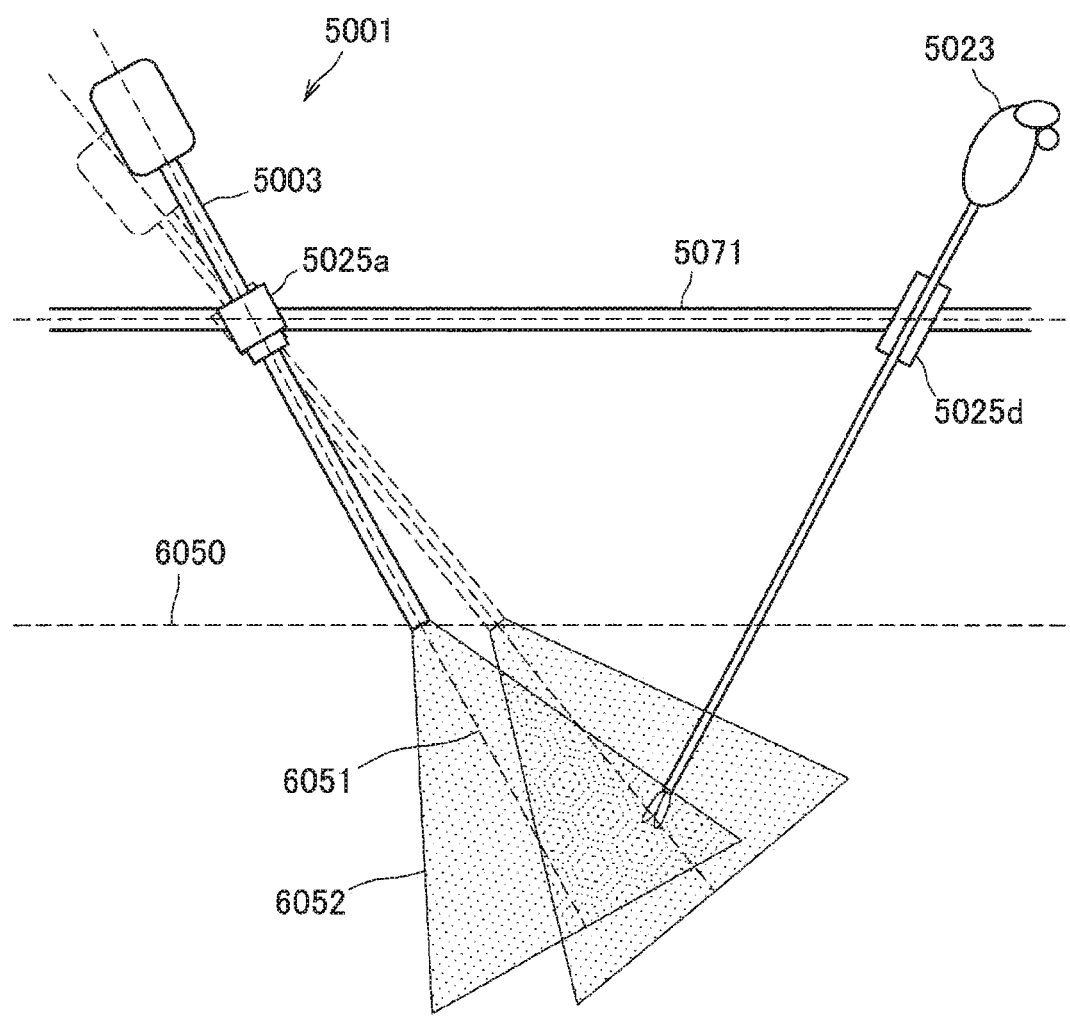
FIG. 21 is a diagram for describing an overview of a second embodiment.
Figure 22:
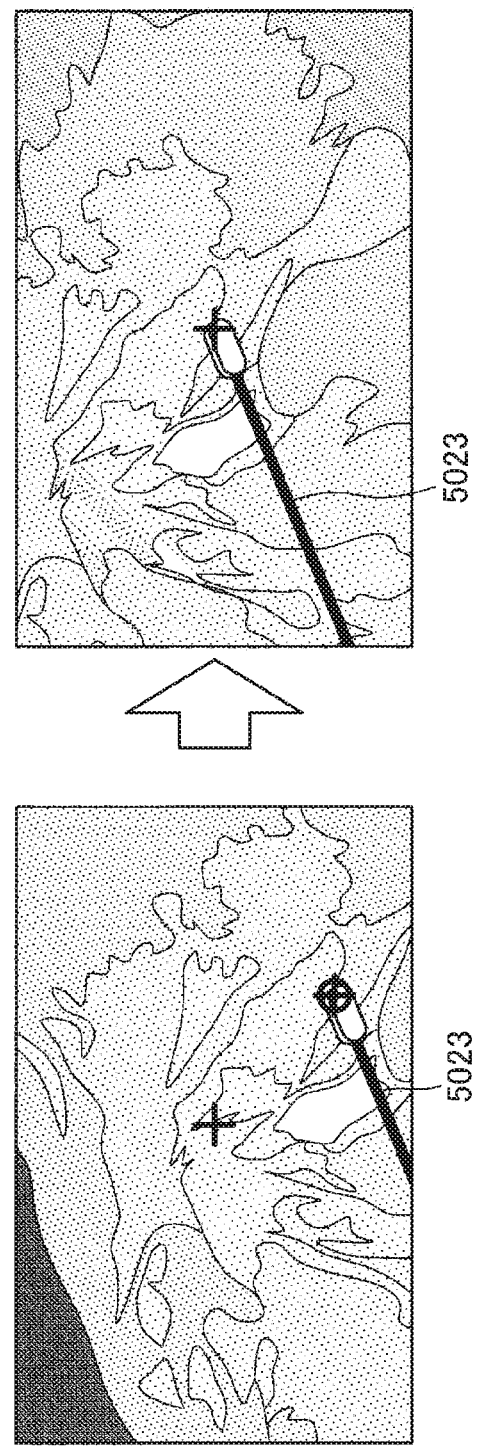
FIG. 22 is a diagram for describing the overview of the second embodiment.

FIGS. 21 and 22 are diagrams for describing the overview of the present embodiment. FIG. 21 illustrates a state where the lens barrel 5003 of the endoscope 5001 is inserted into a body cavity of the patient 5071 through the trocar 5025a tapped in the abdominal wall of the patient 5071. The endoscope 5001 indicated by a solid line represents current position and posture, and the endoscope 5001 illustrated by a broken line represents a position and a posture of a movement destination (in other words, in the future) by endoscope control processing according to the present embodiment is illustrated. Furthermore, the forceps 5023 are inserted from the trocar 5025d tapped into the abdominal wall of the patient 5071. FIG. 22 illustrates images (hereinafter also referred to as endoscopic images) obtained by the endoscope 5001 illustrated in FIG. 21. The left drawing is an image obtained in the current position and posture, and the right drawing is an image obtained after movement by the endoscope control processing according to the present embodiment.

With reference to FIG. 21, a distal end of the forceps 5023 is taken inside a field of view 6052 of the endoscope 5001 in the current position and orientation of the endoscope 5001, but is not present on a central axis (in other words, an optical axis) 6051. Therefore, an endoscopic image in which the distal end of the forceps 5023 has not been reflected at the center can be obtained as illustrated in the left drawing of FIG. 22. In such a situation, the endoscopic surgery system 5000 according to the present embodiment performs a process of moving the endoscope 5001 such that a surgical tool such as the forceps 5023 is reflected at the center of a screen. Specifically, the endoscopic surgery system 5000 moves the endoscope 5001 by the support arm device 5027 (not illustrated) such that the distal end of the forceps 5023 is positioned on the central axis 6051. With the movement, an endoscopic image in which the distal end of the forceps 5023 has been reflected at the center is obtained as illustrated in the right drawing of FIG. 22.

In this manner, the endoscopic surgery system 5000 can automatically follow the surgical tool to provide the endoscopic image in which the surgical tool has been reflected at the center of the screen. Thus, an operator can comfortably continue surgery without interrupting the surgery and operating the endoscope 5001. Furthermore, in a case where an object to be followed is the forceps as described above, it is possible to particularly improve the convenience of the operator since the forceps is frequently used in the surgery.

Moreover, a virtual plane 6050 is set with reference to FIG. 21. The virtual plane 6050 may be, for example, a virtual wall set by the process that has been described in the above-described first embodiment. The endoscopic surgery system 5000 according to the present embodiment constrains the distal end of the endoscope on the virtual plane 6050 and moves the endoscope. With the configuration, the endoscopic surgery system 5000 can automatically follow the surgical tool without bringing the endoscope into contact with an organ. Furthermore, the endoscope distal end is constrained on the virtual plane while the endoscope moves away from an object to be captured (the organ and the surgical tool) only by simply tilting the endoscope, and thus, it is possible to prevent the movement away from the object to be captured.

Note that the virtual plane 6050 may be a curved surface and may be, for example, a curved surface maintaining a predetermined distance from an organ although the virtual plane 6050 is illustrated as a straight line (in other words, a flat surface) in FIG. 21.

Figure 23:
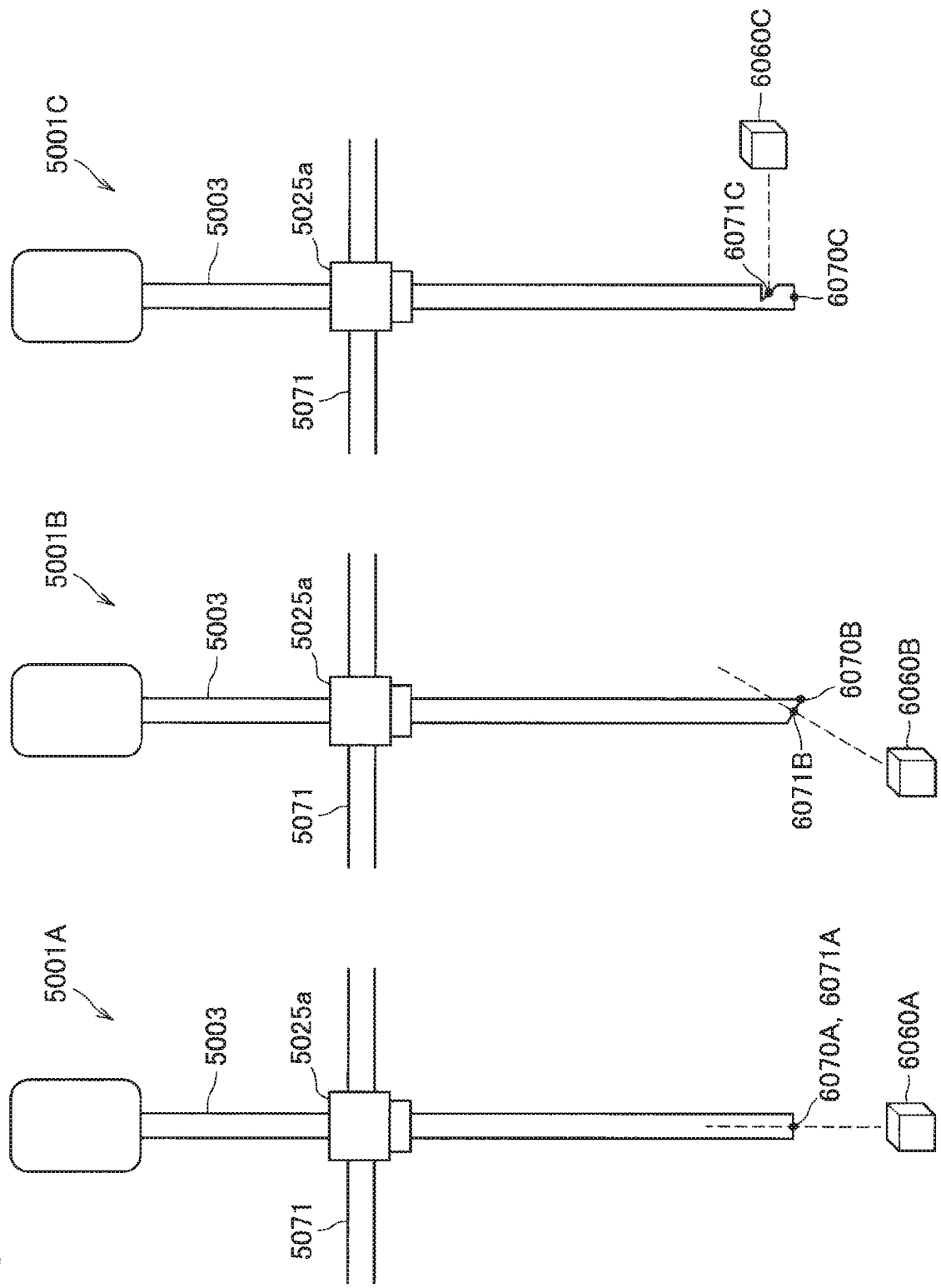
FIG. 23 is a diagram for describing an example of a point to be constrained according to the second embodiment.

Subsequently, an example of a point to be constrained will be described with reference to FIG. 23. FIG. 23 is a diagram for describing an example of the point to be constrained according to the present embodiment. FIG. 23 illustrates a state where the lens barrel 5003 of each of endoscopes 5001A to 5001C is inserted into a body cavity of the patient 5071 through the trocar 5025a tapped in the abdominal wall of the patient 5071. The endoscope 5001A illustrated on the left side of FIG. 23 is a forward-viewing scope in which an object 6060A in a longitudinal direction (in other words, a proceeding direction) of the endoscope is an object to be imaged. The endoscope 5001B illustrated at the center of FIG. 23 is an oblique-viewing scope in which an object 6060B in a direction obliquely shifted from the longitudinal direction of the endoscope is an object to be imaged. The endoscope 5001C illustrated on the right side of FIG. 23 is a side-viewing scope in which an object 6060C in a direction orthogonal to the longitudinal direction of the endoscope (in other words, a side surface of the endoscope) is an object to be imaged. The endoscopic surgery system 5000 may set points 6070A to 6070C at distal ends in the longitudinal direction of the endoscopes 5001A to 5001C as the points to be constrained. In this case, a point that is most likely to contact an organ, the point farthest from the trocar 5025a in a part of the endoscope 5001 inserted into the body cavity of the patient is constrained on the virtual plane, and thus, it is possible to minimize the risk of organ damage. The endoscopic surgery system 5000 may set points 6071A to 6071C on objective lenses of the endoscopes 5001A to 5001C as the point to be constrained. Since the objective lens is typically present near the distal end of the endoscope as illustrated in FIG. 23, the risk of organ damage can be reduced, which is similar to the case of using the endoscope distal end as the point to be constrained. Of course, the point to be constrained is not limited to these examples, and can be an arbitrary point present near the endoscope distal end. Note that a description will be given assuming that the point to be constrained point is the endoscope distal end hereinafter.

Subsequently, an overview of a process of realizing the above-described endoscope control will be described with reference to FIG. 24.

Figure 24:
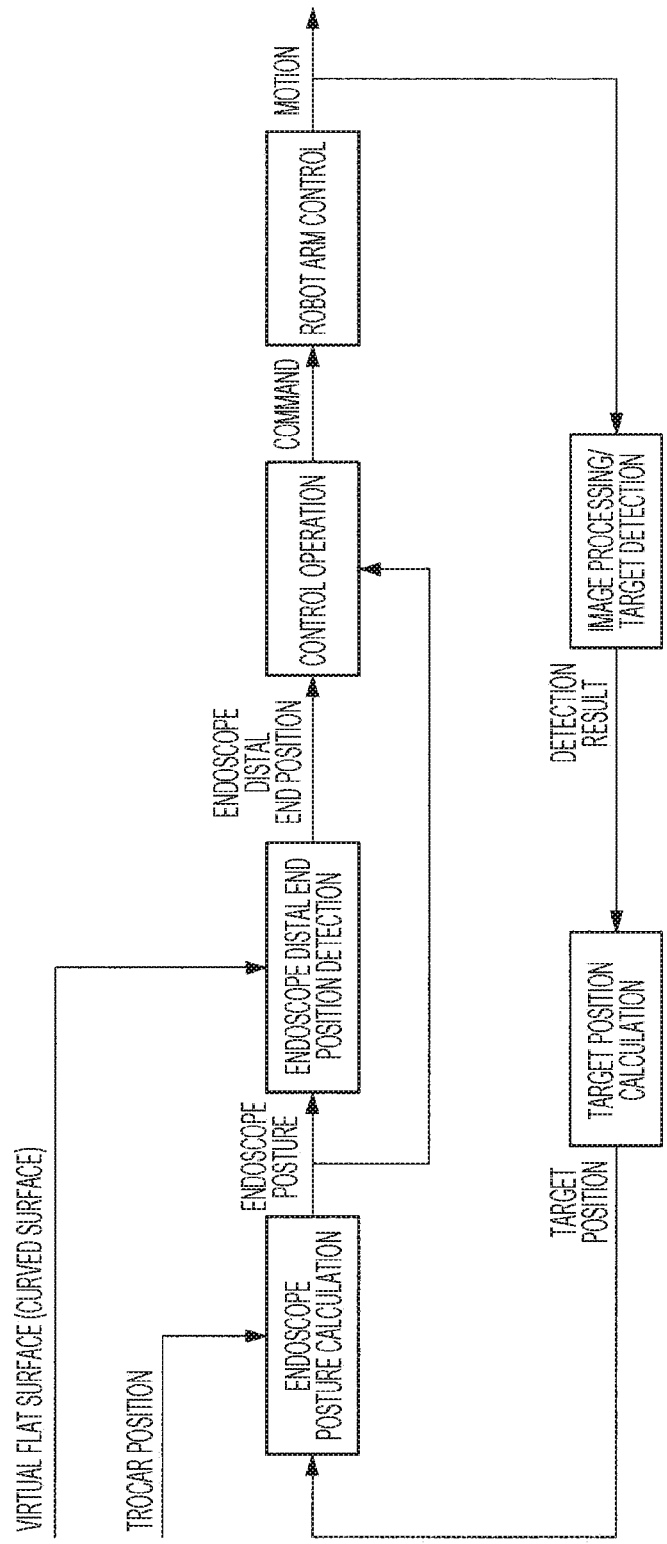
FIG. 24 is a diagram for describing an overview of endoscope control processing according to the second embodiment.

FIG. 24 is a diagram for describing an overview of endoscope control processing according to the present embodiment. Each block illustrated in FIG. 24 represents a process, and the endoscope control processing includes a plurality of processes. As illustrated in FIG. 24, the endoscopic surgery system 5000 performs image processing to detect a target such as a surgical tool. Then, the endoscopic surgery system 5000 calculates a position of the target on the basis of the detection result. Next, the endoscopic surgery system 5000 calculates a current posture of the endoscope on the basis of the calculated target position and trocar position. Next, the endoscopic surgery system 5000 calculates a target endoscope distal end position on the basis of the calculated current posture of the endoscope and setting information of a virtual plane (flat surface or curved surface). Next, the endoscopic surgery system 5000 calculates a change amount of the posture of the endoscope on the basis of the current endoscope posture and the target endoscope distal end position, and generates arm control information (in other words, a command) to realize a posture change in accordance with the calculated change amount. Then, the endoscopic surgery system 5000 controls a robot arm (for example, the arm unit 5031) to operate according to the generated command. The endoscopic surgery system 5000 repeatedly performs the series of processes described above.

<3.2. Details>

Hereinafter, details of the endoscope control processing according to the present embodiment will be described.

(1) Introduction

According to the present embodiment, the endoscopic surgery system 5000 can realize a function of recognizing a surgical tool from an endoscopic image and automatically following the surgical tool. Hereinafter, a description will be given regarding a calculation method in which an arm operates an endoscope from an image-processed part (marker detection) and a detection result to move the surgical tool to the center of a screen while considering a trocar point.

Hereinafter, a method of detecting the surgical tool (marker) by image processing will be described after describing a functional requirement, and then, a calculation method of converting the detection result into target movement information and posture information and performing an operation will be described.

(2.1) Functional Requirement

Assuming an endoscopic surgical operation, the following restrictions are set. It is desirable to operate an arm to realize a continuous operation in which the surgical tool is constantly kept at the center of the screen while observing the following restrictions.

The endoscope is not separated from the trocar point.

To move on a surface (for example, the virtual wall in the first embodiment) set to the endoscope distal end at the start.

2D is used for the endoscopic image.

To enable implementation without calibration of the camera and the endoscope

Note that only the forward-viewing scope will be described and the oblique-viewing scope will not be described hereinafter, but the present technology can of course be applied to the oblique-viewing scope.

(2.2) Image Processing

The endoscopic surgery system 5000 detects a surgical tool (for example, a distal end position and/or a posture of the surgical tool) by image processing.

For example, the position of the surgical tool may be detected by image processing based on an endoscopic image by attaching a marker serving as a mark to the distal end of the surgical tool. It is desirable that the marker be easily detected. For example, the marker may be a color prominent in a body cavity such as blue or green. Furthermore, the marker may be a specific pattern such as a two-dimensional code and a barcode. With the configuration, the endoscopic surgery system 5000 can easily recognize an object to be followed.

For example, the marker to serve as the mark may be attached to a part of the surgical tool exposed outside the body, and the position of the surgical tool may be detected on the basis of a detection result of the marker obtained by an external sensor and information such as a length and a posture of the surgical tool.

Note that the detection of the surgical tool may be performed by a method other than image processing.

For example, a special trocar may be created, and the position of the surgical tool may be calculated on the basis of an insertion amount of the surgical tool and an angle of the trocar.

For example, the surgical tool may be attached to a robot arm other than the endoscope, and the position of the surgical tool may be calculated on the basis of position and posture information of the robot arm.

(2.3) Target Calculation (2.3.1) Overview of Processing

The endoscopic surgery system 5000 performs target calculation. The target calculation is a calculation to calculate both the position and posture and give an instruction on movement.

Specifically, the endoscopic surgery system 5000 first obtains a target position from the image processing result, and then, determines a change amount of a posture on the basis of a current posture using the trocar point as a starting point and a posture at the time of reaching the target position. Furthermore, the endoscopic surgery system 5000 performs the target calculation on the basis of the current position and posture, acquired by an encoder, while obtaining a movement amount from the image processing result, but adds a calculated value to a command value performed last in the case of performing an actual command. A reason for this is because there is a shift between a current value and the command value due to a control error and a problem that an operation is not smoothly performed and the error increases occurs if a goal is set using the current value as the starting point in the case of outputting the command value.

Hereinafter, an example of flow of a target calculation process will be described with reference to FIG. 25.

Figure 25:
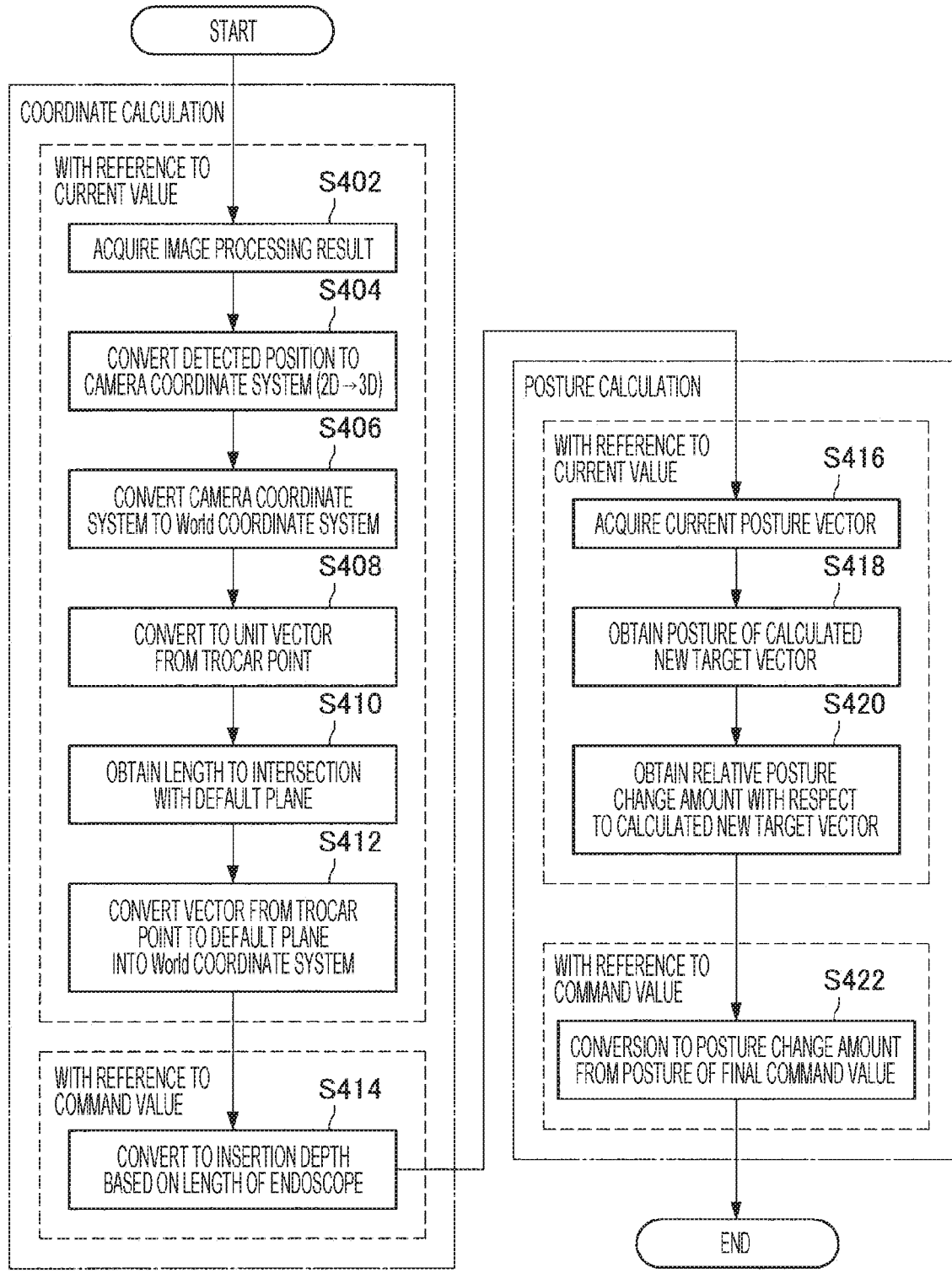
FIG. 25 is a flowchart illustrating an example of flow of a target calculation process by an endoscopic surgery system according to the second embodiment.

FIG. 25 is a flowchart illustrating an example of the flow of the target calculation process by the endoscopic surgery system 5000 according to the present embodiment. As illustrated in FIG. 25, the endoscopic surgery system 5000 first performs coordinate calculation.

In the coordinate calculation, the endoscopic surgery system 5000 first calculates coordinates on the basis of a current value. Specifically, the endoscopic surgery system 5000 acquires an image processing result (step S402). Next, the endoscopic surgery system 5000 converts the detected position into a camera coordinate system (in other words, conversion from 2D to 3D) (step S404). Next, the endoscopic surgery system 5000 converts the camera coordinate system into a world coordinate system (step S406). Next, the endoscopic surgery system 5000 converts a trocar point into a unit vector (step S408). Next, the endoscopic surgery system 5000 obtains a length up to an intersection with a default plane (in other words, the virtual plane) (step S410). Next, the endoscopic surgery system 5000 converts the vector from the trocar point to the predetermined plane into the world coordinate system (step S412).

The endoscopic surgery system 5000 calculates coordinates on the basis of a command value after calculating the coordinates on the basis of the current value. Specifically, the endoscopic surgery system 5000 performs conversion into an insertion depth on the basis of a length of the endoscope (step S414).

After the coordinate calculation, the endoscopic surgery system 5000 performs posture calculation.

In the posture calculation, the endoscopic surgery system 5000 first calculates a posture on the basis of a current value. Specifically, the endoscopic surgery system 5000 acquires a current posture vector (step S416). Next, the endoscopic surgery system 5000 obtains a posture of the calculated new target vector (step S418). Next, the endoscopic surgery system 5000 determines a relative posture change amount with respect to the calculated new target vector (step S420).

The endoscopic surgery system 5000 calculates the posture on the basis of a command value after calculating the posture on the basis of the current value. Specifically, the endoscopic surgery system 5000 performs conversion to the posture change amount from a posture of a final command value (step S422).

With the above-described process, the endoscopic surgery system 5000 obtains the target position and the target posture.

(2.3.2) Target Position Calculation

Figure 26:
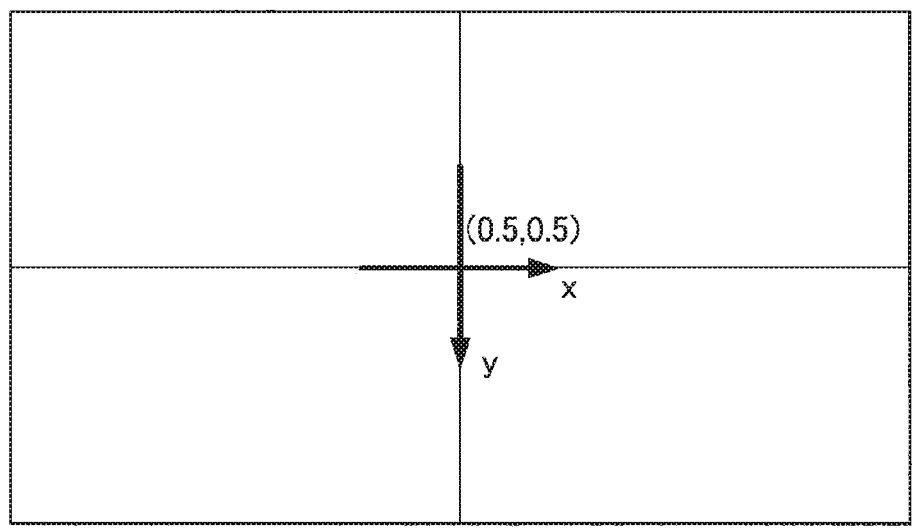
FIG. 26 is a diagram for describing target position calculation according to the second embodiment.

FIG. 26 is a diagram for describing target position calculation according to the present embodiment. As illustrated in FIG. 26, an image processing result is given in notification as a value obtained by normalizing a position, viewed from a camera coordinate system where the center of a screen of a camera distal end is (0.5, 0.5), to [0.0-1.0]. Since the value is a dimensionless value as it is, the endoscopic surgery system 5000 first converts the value into a system in units of meters. However, the endoscopic surgery system 5000 assumes a depth as, for example, 50 [mm] during conversion since the image processing result is 2D and there is no information in a depth direction, and sets a virtual position in combination with an angle of view.

Reasons why the depth is assumed to be 50 [mm] will be described. A first reason is because a movement amount of (x,y) becomes greater than the actual (x,y) and overruns (oscillates) if the assumed value is greater than an actual value. A second reason is because an imaging distance in an assumed surgical technique is set to 50 [mm] to 100 [mm] as the minimum distance. A third reason is because it is possible to finally reach the goal since the movement is newly determined from a residual in the next image processing result in a case where an actual distance is greater.

Furthermore, the following Formulas (2) to (4) are used in order to convert dimensionless values (x,y) into metric units (X,Y,Z).

[Formula 2]
$$X = z_{const}\left(x - \frac{1}{2}\right)\tan\frac{\theta}{2} \quad (2)$$

[Formula 3]
$$Y = z_{const}\left(y - \frac{1}{2}\right)\tan\frac{\theta}{2} \quad (3)$$

[Formula 4]
$$Z = z_{const} \quad (4)$$

However, $z_{const}$ is an assumed depth distance (0.05 in this example).

The camera coordinate system and a final axis (camera yaw axis) of the arm are attached in the state of being rotated by any of 0 degrees, ±90 degrees, and 180 degrees about the z axis. For example, in a case where the both are attached in the state of being rotated by 180 degrees, a rotation matrix about the z axis is applied to add a length L of the endoscope in the z-axis direction, thereby performing conversion to a position $P_{Camera}$ Yaw viewed from a coordinate system of the camera yaw axis.

[Formula 5]

$$P_{camera\ Yaw} = \begin{pmatrix} \cos\pi & -\sin\pi & 0 \\ \sin\pi & \cos\pi & 0 \\ 0 & 0 & 1 \end{pmatrix}\begin{pmatrix} X \\ Y \\ Z \end{pmatrix} + \begin{pmatrix} 0 \\ 0 \\ L \end{pmatrix} = \begin{pmatrix} -X \\ -Y \\ Z+L \end{pmatrix} \quad (5)$$

The endoscopic surgery system 5000 moves the camera such that an object matches on the optical axis of the camera in order to make the object is reflected in the central portion of an endoscopic image on the basis of the obtained position of the object. At that time, in the case of the endoscope, it is desirable to perform an operation while considering two constraint conditions, that is, preventing the endoscope from deviating from the trocar point and causing the distal end to operate on a plane set at the start of the operation. Therefore, the endoscopic surgery system 5000 obtains an intersection with a designated plane on a line connecting the trocar point and the position of the object as a target position of the distal end. The endoscopic surgery system 5000 performs such calculation, for example, as follows.

It is assumed that a unit vector in a direction from the object to the trocar point, viewed from a camera coordinate system $O_c$, is $w_c$, the position of the object is $q_c$, and the origin of the default plane is $O_p$. At this time, a point q' intersecting an $O_p$ plane viewed from $O_c$ is set as $q'=q_c+\alpha w_c$ (a is a scalar value that defines a length of a vector). Here, in a case where q' is viewed from $O_p$ in order to obtain α, it is used that z of q' is zero. Therefore, when this value is set as $q'_p$, $q'_p$ is expressed as the following formula.

[Formula 6]

$$q'_p = q_p + \alpha w_p \quad (6)$$

From this relational expression, an equation that allows z of $q'_p$ to be zero is expressed as the following formula.

[Formula 7]

$$z(q_p) + \alpha z(w_p) = 0 \quad (7)$$

Here, z(·) is a function that takes a value of z of a vector. If the above Formula (7) is solved for α, the following formula is derived.

[Formula 8]

$$\alpha = -\frac{z(q_p)}{w(q_p)} \quad (8)$$

When the above Formula (8) is combined with $q'_c$ the following Formula is derived.

[Formula 9]

$$q'_c = q_c - \frac{z(q_p)}{z(w_p)} w_c \quad (9)$$

The target position is $q'_c$ illustrated in the above formula (9) becomes the target position.

The target position is determined with reference to the current value, but the command value is commanded as a relative displacement amount with reference to the final command value. Therefore, when a distal end position $p_c$ as the current value, the obtained value $q'_c$, and the final command value p are used, a new command value p' is expressed by the following formula.

[Formula 10]

$$p' = p + (q'_c - p_c) \quad (10)$$

(2.3.3) Target Posture Calculation

The endoscopic surgery system 5000 obtains a target posture after setting the target position. Since $w_p$ is already present as information regarding the target posture, a posture can be obtained as in the following formula using quaternions from this $w_p$ and a unit vector $v_p$ of a current posture. Hereinafter, it is assumed that values obtained by converting $w_p$ and $v_p$ to quaternions are $q_w$ and $q_v$, respectively. Note that $q_w$ and $q_v$ in this section have the same signs as $q_w$ and $q_v$ in (3.3.2), but have different meanings.

[Formula 11]

$$q_w = (0; -w_p) \quad (11)$$

[Formula 12]

$$q_v = (0; v_p) \quad (12)$$

A reason why the sign of $w_p$ is negative in $q_w$ is because an original vector is a vector in a direction from the position of the object to the trocar, and the negative sign has been applied for the purpose of reversing the direction. A product of the values obtained by converting the vectors to the quaternions has a real part where an inner product of the vectors of imaginary parts has an inverted sign, and an imaginary part is a cross product of the two vectors. Furthermore, it is known that the cross product becomes a rotation axis orthogonal to the two vectors.

Therefore, assuming that an angle formed by the two vectors is θ and a result of the cross product is u, it is sufficient to perform rotation by θ with u as the rotation axis on the basis of the relationship of the following formula.

[Formula 13]

$$q_v q_w = (-\cos\theta; u) \quad (13)$$

[Formula 14]

$$\|u\| = \sin\theta \quad (14)$$

Therefore, a quaternion $q_r$ which represents rotation using these two is expressed by the following formula.

[Formula 15]

$$q_r = \left(\cos\frac{\theta}{2}; u\sin\frac{\theta}{2}\right) \quad (15)$$

Similarly to the target position, a calculation result of $q_r$ is also obtained with reference to a current posture, but a command value is calculated as a change from a final command value. This command value is expressed by the following formula using p.

[Formula 16]

$$q_r\left(0; \frac{p}{\|p\|}\right)\hat{q}_r \quad (16)$$

(3) Implementation Environment

When an operation experiment was actually carried out using the method that has been described so far, a favorable operation result was obtained. Therefore, a configuration and an environment used for the experiment will be described hereinafter.

(3.1) Adjustment Parameter

Before conducting an operation with an actual device, some parameters relating to the operation were adjusted. Here, the parameters and final values will be described.

(3.1.1) Image Processing Cycle

An image itself is updated at a cycle of 60 [Hz]. However, when a target was actually updated at this cycle, divergent vibration occurred and it was difficult to perform a stable operation. Causes are conceivable as follows.

High-speed movement is performed to complete the movement by the next update cycle Movement is fast, an image is blurred, and a processing result becomes unstable A sensitive reaction is made even against noise As a countermeasure, it was considered to add a maximum speed limit, for example. Then, a stable operation was finally realized by dropping the image update cycle to 5 [Hz].

(3.1.2) Follow-up Amount for Each Update

A follow-up operation is an operation to perform movement to a position determined on the basis of an image processing result until an update value of the next image processing result is input. Ideally, it is desirable to be completely located at a position as the previous result at the time of the next update. However, the position obtained by image processing is set using the depth direction for an imaginary distance in this case, and thus, it was expected that an error would be great. Therefore, a progressing amount (in other words, a follow-up amount) by the next update timing for one image processing result is set to half of an ideal target position. That is, an operation similar to that in a case of halving the image processing cycle is performed. Furthermore, such setting of the follow-up amount was performed in expectation of the same effect as that of a case where a gain in control of P is set to 0.5.

(3.1.3) Speed Limit

As described above, the movement amount for one image processing result is adjusted so as to approach a distance which is half of the entire distance until the next image processing result is updated. However, in a case where a marker once leaves out of a screen and then is reflected on the screen again, a movement distance is large so that movement speed increases regardless of any means. For example, if an endoscope operating near an organ in a body cavity of a patient operates at an extremely high speed, a danger of contact or anxiety can occur. Therefore, the endoscopic surgery system 5000 limits a movement speed of an endoscope distal end to a predetermined speed or less. This can reduce the risk or anxiety that the endoscope is brought into contact with an organ in a patient's body cavity.

Since the trocar point is used as the constraint point in this method, a position of the distal end does not significantly change, but a posture thereof significantly changes. Therefore, the speed limitation was performed such that a change rate of the posture was 10 [deg/s] or lower at the maximum. As a result, even in a case where the marker enters from the outside of the screen, it has become possible to alleviate a rapid motion and perform a stable operation.

The settings of the adjustment parameters described above are summarized in the following Table 1.

TABLE 1

| ADJUSTMENT PARAMETER | |
|---|---|
| IMAGE PROCESSING CYCLE | 5 [Hz] |
| FOLLOW-UP AMOUNT FOR EACH UPDATE | 50 [%] OF WHOLE |
| SPEED LIMIT | MAXIMUM 10 [deg/s] |

(3.1.4) Setting of CCU

Since image processing is affected by image creation of a camera, the used CCU was set to auto exposure, and 3200 [K], adjusted using a white balance adjustment function immediately before the experiment, was used as white balance. Although experiments were conducted in two different experimental environments, the influence of the connected light source device was dominant in both the cases, and thus, both the cases exhibited favorable operations with the same parameters.

(4) Cancellation of Constraint

The endoscopic surgery system 5000 may cancel the constraint of the point to be constrained on the virtual plane. For example, the endoscopic surgery system 5000 may cancel the constraint of the point to be constrained on the virtual plane with a trigger that the arm unit 5031 receives an external force from a user and the arm control device 5045 performs power assist control. Furthermore, the endoscopic surgery system 5000 may cancel the constraint of the point to be constrained on the virtual plane with a trigger of an instruction from an operator to cancel the constraint by a voice input or an input to a button (not illustrated) or the like. The endoscopic surgery system 5000 cancels the point to be constrained on the virtual plane in a case where an operation different from an operation for treatment in a body cavity is performed such as a case where the robot arm is no longer used in surgery and a case where the endoscope 5001 is taken out of a body cavity of a patient for replacement, cleaning, or the like of the endoscope. With the configuration, it becomes possible not to keep hindering the surgery in a case where a reason for constraining the point to be constrained on the virtual plane disappears.

(5) Operation by Operator

The endoscopic surgery system 5000 controls the arm unit 5031 on the basis of an operation input from an operator. For example, the endoscopic surgery system 5000 may drive the arm unit 5031 on the basis of an operation input to the input device 5047 (including the foot switch 5057), a button (not illustrated), or the like from the operator 5067 and control the position and posture of the endoscope 5001. The arm unit 5031 may be operated in a so-called master-slave manner, and in this case, the arm unit 5031 can be remotely operated by the user via the input device 5047 installed at a place distant from the operating room. Furthermore, the endoscopic surgery system 5000 may perform so-called power assist control in which the arm unit 5031 is controlled on the basis of an external force from the user.

The endoscopic surgery system 5000 constrains the point to be constrained of the endoscope 5001 on the virtual plane even at the time of controlling the arm unit 5031 on the basis of the operation input from the operator. With the configuration, the operator can freely move the endoscope 5001 while constraining the point to be constrained of the endoscope 5001 on the virtual plane, and thus, the convenience of the operator is improved. Moreover, since the point to be constrained of the endoscope 5001 is constrained on the virtual plane, it is possible to prevent the distance from the endoscope 5001 to the object from being too close or too far and an accompanying shift of the focus. Furthermore, since the point to be constrained of the endoscope 5001 is constrained on the virtual plane, it is possible to mitigate the risk of organ damage.

The operation input from the operator may be a voice input. For example, when the operator gives an instruction on up, down, left, or right with voice while viewing a screen of an endoscopic image, the endoscopic surgery system 5000 controls the position and posture of the endoscope 5001 so as to obtain the endoscopic image in the direction given in instruction while constraining the point to be constrained of the endoscope 5001 on the virtual plane. With the configuration, the operator can freely move the endoscope 5001 only by the voice input, and thus, an operation to once place a surgical tool in order for an operation input using the hand to the endoscope 5001 become unnecessary, for example, and the convenience of the operator is further improved. Moreover, since the point to be constrained of the endoscope 5001 is constrained on the virtual plane, it is possible to prevent the distance from the endoscope 5001 to the object from being too close or too far and an accompanying shift of the focus. Furthermore, since the point to be constrained of the endoscope 5001 is constrained on the virtual plane, it is possible to mitigate the risk of organ damage.

(6) Supplement

In the above description, the technology in which the endoscopic surgery system 5000 controls the arm unit 5031 such that the object is present on the optical axis of the endoscope 5001 so as to make the object present at the center of the image obtained by the endoscope has been described in detail, but the present technology is not limited to such an example. For example, the endoscopic surgery system 5000 may control the arm unit 5031 such that an object is present near the optical axis of the endoscope 5001. With the configuration, it becomes possible to make the object present near the center of the image obtained by the endoscope. Note that a specific value of an allowable shift from the optical axis to the object (an angular difference with the trocar point as the origin) is arbitrary, but can vary depending on the magnification of the endoscope 5001, the distance to the object, and the like.

(7) Summary

In the present embodiment, the description has been given regarding the function of detecting the marker on the endoscopic image and continuing the follow-up such that a position of the marker is located at the screen center and the experiments of the function. Further, the calculation method in which the trocar point and the default plane are considered has been used for the calculation of the target position and the target posture. Then, the results of the experiments have shown that the follow-up with respect to the marker is possible.

4. Summary

Hereinabove, one embodiment of the present disclosure has been described in detail with reference to FIGS. 1 to 26.

The endoscopic surgery system 5000 according to the first embodiment calculates the relative positional relationship between the distal end of the surgical instrument, attached to the medical robot arm and inserted into the patient's body, and the patient, and sets the movable range of the surgical instrument inside the patient's body in the distal end coordinate system of the surgical instrument on the basis of the calculation result of the relative positional relationship. When control is performed such that the object (for example, the surgical instrument such as the endoscope and the surgical tool) does not come out of the movable region on the basis of such settings, it is possible to mitigate the risk of organ damage. Moreover, since it is possible to freely move the surgical instrument in a range that does not exceed the movable region, the convenience of the operator is improved.

The endoscopic surgery system 5000 according to the second embodiment sets the virtual plane inside the patient's body, controls the medical robot arm such that the object present inside the patient's body matches on the optical axis of the endoscope attached to the medical robot arm and inserted into the patient's body, and moves the endoscope while constraining the distal end of the endoscope on the virtual plane. With the control, it becomes possible to take an object such as a surgical instrument and a tumor into the central portion of the image obtained by the endoscope, and the convenience of the operator is improved. Moreover, the appropriate virtual plane (for example, the virtual wall described in the first embodiment) is set, it is possible to mitigate the risk of organ damage.

Although the preferred embodiments of the present disclosure have been described as above in detail with reference to the accompanying drawings, a technical scope of the present disclosure is not limited to such examples. It is apparent that a person who has ordinary knowledge in the technical field of the present disclosure can find various alterations and modifications within the scope of technical ideas described in the claims, and it should be understood that such alterations and modifications will naturally pertain to the technical scope of the present disclosure.

Note that the series of processes performed by the respective devices described in the present specification may be realized using any of software, hardware, and a combination of software and hardware. Programs constituting the software are stored in advance in, for example, storage media (non-transitory media) provided inside or outside the respective devices. Then, each of the programs is read into a RAM at the time of execution by a computer, for example, and is executed by a processor such as a CPU.

Furthermore, the processes described using the flowchart and the like in the present specification are not necessarily executed in the illustrated order. Some processing steps may be performed in parallel. Furthermore, additional processing steps may be employed and some processing steps may be omitted.

Furthermore, the effects described in the present specification are merely illustrative or exemplary, and are not limited. That is, the technology according to the present disclosure can exhibit other effects apparent to those skilled in the art on the basis of the description of the present specification, in addition to or instead of the above-described effects.

Note that the following configurations also pertain to the technical scope of the present disclosure.

(1) A medical arm system including:

a multi-joint arm which has a plurality of links connected by joints and a distal end to which an endoscope is connectable; and a control unit which sets a virtual plane in a body cavity of a patient and controls the multi-joint arm so as to constrain a predetermined point in the body cavity on the virtual plane in the endoscope.

(2) The medical arm system described in (1), in which the control unit controls the multi-joint arm such that an observation object in the body cavity is present in a central region of an image obtained by the endoscope.

(3) The medical arm system described in (2), in which the observation object is a surgical tool.

(4) The medical arm system described in (3), in which the observation object is forceps.

(5) The medical arm system described in (3) or (4), in which the observation object is a marker attached to the surgical tool.

(6) The medical arm system described in any one of (1) to (5), in which the control unit limits a movement speed of the predetermined point to a predetermined speed or lower.

(7) The medical arm system described in any one of (1) to (6), in which the control unit releases the constraint of the predetermined point on the virtual plane.

(8) The medical arm system described in any one of (1) to (7), in which the control unit controls the multi-joint arm on the basis of an operation input from an operator.

(9) The medical arm system described in (8), in which the operation input is a voice input.

(10) The medical arm system described in any one of (1) to (9), in which the predetermined point is a point at a distal end of the endoscope in a longitudinal direction.

(11) The medical arm system described in any one of (1) to (10), in which the control unit sets a region distant from an organ in the body cavity by a predetermined distance as a movable region of a surgical instrument connected to the multi-joint arm.

(12) The medical arm system described in (11), in which a boundary defining the movable region is the virtual plane.

(13) The medical arm system described in (12), in which the control unit sets the virtual plane on the basis of shape data in the body cavity.

(14) The medical arm system described in (13), in which the shape data is a computed tomography (CT) image or a magnetic resonance imaging (MRI) image.

(15) The medical arm system described in any one of (12) to (14), in which the control unit sets the virtual plane on the basis of an abdominal circumference of the patient.

(16) The medical arm system described in any one of (12) to (15), in which the control unit sets the virtual plane in a direction in which an operation range of the surgical instrument is narrowed during surgery.

(17) The medical arm system described in (16), in which the control unit sets the virtual plane according to a distance from a distal end of the endoscope.

(18) The medical arm system described in (17), in which the endoscope includes a distance measurement sensor.

(19) The medical arm system described in (18), in which the control unit sets a distance, obtained by subtracting an endoscope minimum distance of the endoscope from a distance from a distal end of the endoscope to an organ measured by the distance measurement sensor, as a setting distance of the virtual plane.

(20) A control device including a control unit which sets a virtual plane in a body cavity of a patient and controls a multi-joint arm, which has a plurality of links connected by joints and a distal end to which an endoscope is connectable, so as to constrain a predetermined point in the body cavity on the virtual plane in the endoscope.

(21) A control method executed by a processor, the control method including:
setting a virtual plane in a body cavity of a patient; and
controlling a multi-joint arm, which has a plurality of links connected by joints and a distal end to which an endoscope is connectable, so as to constrain a predetermined point in the body cavity on the virtual plane in the endoscope.

REFERENCE SIGNS LIST

5000 Endoscopic surgery system
5001 Endoscope
5003 Lens barrel
5005 Camera head
5007 Lens unit
5009 Imaging unit
5011 Drive unit
5013 Communication unit
5015 Camera head control unit
5017 Surgical tool
5019 Insufflation tube
5021 Energy treatment tool
5023 Forceps
5025 Trocar
5027 Support arm device
5029 Base unit
5031 Direct arm unit
5031 Arm unit
5033 Joint
5035 Link
5037 Cart
5039 Camera control unit
5041 Display device
5043 Light source device
5045 Arm control device
5047 Input device
5049 Treatment tool control device
5051 Insufflation device
5053 Recorder
5055 Printer
5057 Foot switch
5059 Communication unit
5061 Image processing unit
5063 Control unit
5065 Transmission cable
5067 Operator
5069 Patient bed
5071 Patient
6000 Position measurement device
6001 Marker
6002 Marker

The invention claimed is:

1. A medical arm system, comprising:
a multi-joint arm that includes:
a plurality of links connected by joints; and
a distal end to which an endoscope is connectable; and
a control unit configured to:
set, as a movable region of the endoscope connected to the multi-joint arm, a region distant by a specific distance from an organ in a body cavity of a body;
set a boundary of the movable region as a virtual plane in the body cavity; and
control the multi-joint arm to constrain a specific point of the endoscope on the virtual plane.

2. The medical arm system according to claim 1, wherein the endoscope includes an observation object,
the endoscope obtains an image of the body cavity, and
the control unit is further configured to control the multi-joint arm such that the observation object in the body cavity is present in a central region of the image obtained by the endoscope.

3. The medical arm system according to claim 2, wherein the observation object is a surgical tool.

4. The medical arm system according to claim 3, wherein the observation object is forceps.

5. The medical arm system according to claim 3, wherein the observation object is a marker attached to the surgical tool.

6. The medical arm system according to claim 1, wherein the control unit is further configured to limit a movement speed of the specific point to one of a specific speed or lower.

7. The medical arm system according to claim 1, wherein the control unit is further configured to release the constraint of the specific point on the virtual plane.

8. The medical arm system according to claim 1, wherein the control unit is further configured to control the multi-joint arm based on an operation input from an operator.

9. The medical arm system according to claim 8, wherein the operation input is a voice input.

10. The medical arm system according to claim 1, wherein the specific point is at a distal end of the endoscope in a longitudinal direction.

11. The medical arm system according to claim 1, wherein the control unit is further configured to set the virtual plane based on shape data associated with the body cavity.

12. The medical arm system according to claim 11, wherein the shape data is one of a computed tomography (CT) image or a magnetic resonance imaging (MRI) image.

13. The medical arm system according to claim 1, wherein the control unit is further configured to set the virtual plane based on an abdominal circumference of the body.

14. The medical arm system according to claim 1, wherein the control unit is further configured to set the virtual plane in a direction in which an operation range of a surgical instrument is narrowed.

15. The medical arm system according to claim 14, wherein the control unit is further configured to set the virtual plane based on a distance from a distal end of the endoscope.

16. The medical arm system according to claim 15, wherein the endoscope comprises a distance measurement sensor.

17. The medical arm system according to claim 16, wherein
the distance measurement sensor is configured to measure a first distance from the distal end of the endoscope to the organ in the body cavity, and
the control unit is further configured to:
obtain a second distance by subtraction of an endoscope minimum distance of the endoscope from the first distance; and
set the second distance as a setting distance of the virtual plane.

18. A control device, comprising:
a control unit configured to:
set, as a movable region of an endoscope connected to a multi-joint arm, a region distant by a specific distance from an organ in a body cavity of a body;
set a boundary of the movable region as a virtual plane in the body cavity; and
control the multi-joint arm to constrain a specific point of the endoscope on the virtual plane, wherein the multi-joint arm includes:
a plurality of links connected by joints, and
a distal end connectable to the endoscope.

19. A control method, comprising:
setting, as a movable region of an endoscope connected to a multi-joint arm, a region distant by a specific distance from an organ in a body cavity of a body;
setting a boundary of the movable region as a virtual plane in the body cavity; and
controlling the multi-joint arm to constrain a specific point of the endoscope on the virtual plane, wherein the multi-joint arm includes:
a plurality of links connected by joints, and
a distal end connectable to the endoscope.

* * * * *